US012690760B2

(12) United States Patent (10) Patent No.: US 12,690,760 B2
Kawakami (45) Date of Patent: Jul. 28, 2026

(54) INSERTION INSTRUMENT

(71) Applicant: OLYMPUS MEDICAL SYSTEMS CORP., Tokyo (JP)

(72) Inventor: Takumi Kawakami, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 418 days.

(21) Appl. No.: 18/207,232

(22) Filed: Jun. 8, 2023

(65) Prior Publication Data

US 2023/0414087 A1 Dec. 28, 2023

Related U.S. Application Data

(60) Provisional application No. 63/355,225, filed on Jun. 24, 2022.

(51) Int. Cl.
*A61B 1/12* (2006.01)
*A61B 1/06* (2006.01)
*A61B 1/307* (2006.01)
*A61B 18/26* (2006.01)
*A61B 17/22* (2006.01)
*A61B 18/00* (2006.01)

(52) U.S. Cl.
CPC ............ *A61B 1/128* (2013.01); *A61B 1/0684* (2013.01); *A61B 1/307* (2013.01); *A61B 18/26* (2013.01); *A61B 2017/22079* (2013.01); *A61B 2018/00023* (2013.01); *A61B 2018/00511* (2013.01); *A61B 2018/00982* (2013.01)

(58) Field of Classification Search
CPC ............ A61B 1/00066; A61B 1/00068; A61B 1/00119; A61B 1/0052; A61B 1/0053; A61B 1/015; A61B 1/0669; A61B 1/0684; A61B 1/07; A61B 1/125; A61B 1/128; F21V 29/56; F21V 29/57; F21V 29/58; F21V 29/59; G02B 6/4268; G02B 6/4269; G02B 6/4271; G02B 6/4272
See application file for complete search history.

(56) References Cited

U.S. PATENT DOCUMENTS 4,363,080 A * 12/1982 Sylvester ............. A61B 1/0669
362/373
8,622,896 B1 * 1/2014 Termanini ............ A61B 1/0684
600/179

(Continued)

FOREIGN PATENT DOCUMENTS

GB 1393699 A * 5/1975 ......... A61B 1/00165
JP 2007-007322 A 1/2007

(Continued)

*Primary Examiner* — Michael J Carey
*Assistant Examiner* — Stephen Floyd London
(74) *Attorney, Agent, or Firm* — Morgan, Lewis & Bockius LLP

(57) ABSTRACT

An insertion instrument comprises an insertion portion, an operation portion located proximally relative to the insertion portion. The operation portion includes a housing having an exterior body, a light source apparatus located inside the exterior body, a conduit for a fluid. The conduit includes a first portion located outside the exterior body, a second portion located inside the exterior body and in contact with an outer surface of the light source apparatus.

20 Claims, 25 Drawing Sheets

(56) References Cited

U.S. PATENT DOCUMENTS

| | | | | |
|---|---|---|---|---|
| 2003/0163025 A1* | 8/2003 | Kaji | .................... | A61B 1/00128 |
| | | | | 600/156 |
| 2009/0154192 A1* | 6/2009 | Krattiger | ............ | G02B 23/2469 |
| | | | | 362/574 |
| 2011/0034773 A1* | 2/2011 | Ishigami | ................ | A61B 1/128 |
| | | | | 600/160 |
| 2014/0005482 A1* | 1/2014 | Ohara | ................ | A61B 1/00112 |
| | | | | 600/158 |
| 2015/0282701 A1* | 10/2015 | Oskin | .................... | A61B 1/128 |
| | | | | 600/131 |
| 2016/0038013 A1* | 2/2016 | Czupalla | ............ | A61B 1/00142 |
| | | | | 128/849 |
| 2016/0353984 A1* | 12/2016 | Shirota | ................. | H01L 23/467 |
| 2019/0029508 A1* | 1/2019 | Tabata | ................. | A61B 1/0676 |
| 2019/0298162 A1* | 10/2019 | Kudo | .................... | A61B 1/0676 |
| 2020/0379247 A1* | 12/2020 | Pascale | .............. | F28D 15/0275 |
| 2021/0235981 A1* | 8/2021 | McLean | ............ | G02B 23/2476 |

FOREIGN PATENT DOCUMENTS

| | | | |
|---|---|---|---|
| JP | 2010-200944 A | 9/2010 |
| JP | 5993215 B2 | 9/2016 |
| JP | 6210764 B2 | 10/2017 |

\* cited by examiner

FIG. 26

INSERTION INSTRUMENT

RELATED APPLICATION DATA

This application is based on and claims priority under 35 U.S.C. § 119 to U.S. Provisional Application No. 63/355,225 filed on Jun. 24, 2022, the entire contents of which are incorporated herein by reference.

FIELD OF DISCLOSURE

The present disclosure relates to an insertion instrument in which a light source is provided in an operation portion.

BACKGROUND

Conventionally, an insertion instrument, such as an endoscope, has had a configuration in which light from an illumination or therapeutic light source mounted in external equipment, such as a video processor or a light source apparatus, is transmitted from a connector, connected to the external equipment, to a distal end of an insertion portion by means of a light guide, an optical fiber. An insertion instrument having such a configuration is disclosed in Japanese Patent Application Laid-Open Publication No. 2010-200944, for example.

SUMMARY OF THE DISCLOSURE

An insertion instrument according to an aspect of the present disclosure includes: an insertion portion, an operation portion located proximally relative to the insertion portion. The operation portion includes a housing having an exterior body, a light source apparatus located inside the exterior body, a conduit for a fluid. The conduit includes a first portion located outside the exterior body, a second portion located inside the exterior body and in contact with an outer surface of the light source apparatus.

BRIEF DESCRIPTION OF THE DRAWINGS

FIG. 26 is a perspective view, as viewed from a left side, showing the inside of the operation portion of the endoscope of the eighth modification, the operation portion being provided with the base plate.

DETAILED DESCRIPTION

In recent years, for endoscopes being insertion instruments, a type of endoscope has been introduced which does not use a light source, such as a halogen lamp, but mounts a light emitting diode (LED) in the endoscope. An LED has a size smaller than a size of a conventional light source. Therefore, there are cases in which an LED is mounted in an operation portion of an endoscope.

Further, in recent years, there has been a technique for treating stones, such as transurethral lithotripsy in which an endoscope is inserted through a urethra and a stone is crushed by laser under observation through the endoscope. In the transurethral lithotripsy, for example, a ureteroscope (video uretero-renoscope), which can feed and suction liquid, is used in liquid, and a stone is crushed by laser, and is then suctioned and recovered together with the liquid.

For such endoscopes including the ureteroscope, a single-use type endoscope has been considered that is disposed of without having reprocessing treatment after the endoscope is used. Therefore, a single-use endoscope may be an inexpensive structure.

It is an object of the present disclosure to allow an insertion instrument, such as an endoscope, to have a structure that can cool heat generating components in the operation portion at a low cost by using a functional component that is originally included in the insertion instrument.

EMBODIMENT

Hereinafter, the description will be made by taking an endoscope as an example of an insertion instrument of the present embodiment. In the description made hereinafter, drawings based on respective embodiments are schematic views. Note that a relationship between thicknesses and widths of respective components and a ratio between the thicknesses of the respective components, for example, may differ from actual ones. The relationship or the ratio of dimensions may be partially different between drawings.

First, a schematic configuration of an endoscope 1, being an insertion instrument, will be described. The endoscope 1 of the present embodiment has a configuration applicable to various endoscopes, such as esophagogastroduodenoscopes, colonoscopes, bronchoscopes, or video uretero-renoscopes. The endoscope 1 may be of a single-use type that is disposed of after being used, or may be a reusable type that is used again by performing reprocessing treatment after being used.

Figure 1:
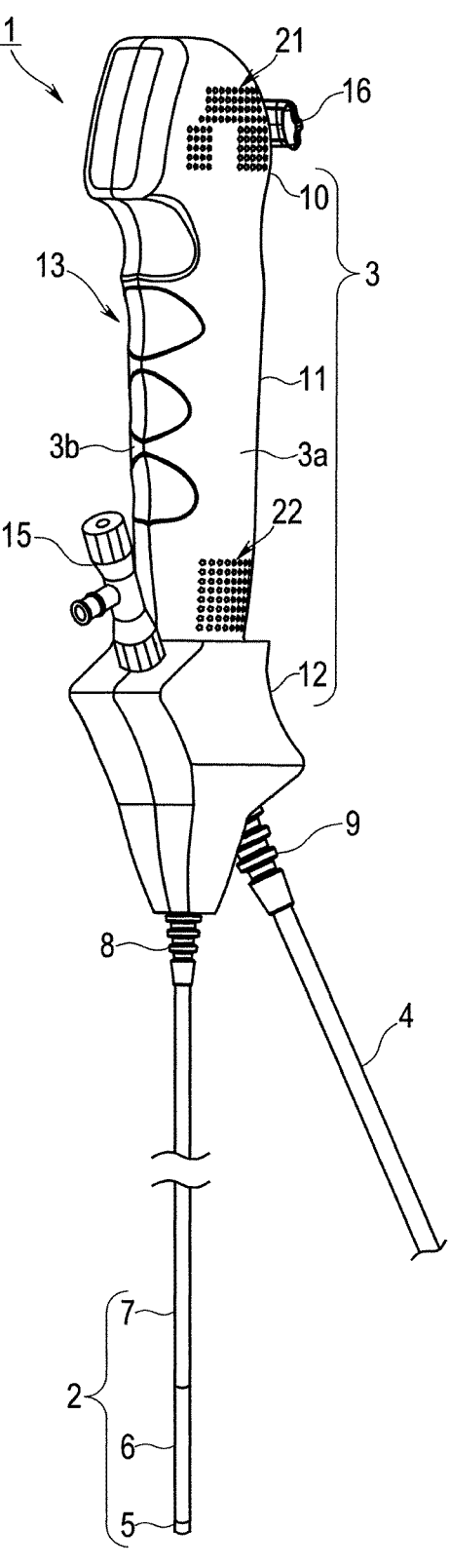
FIG. 1 is a perspective view showing an endoscope being an insertion instrument.

As shown in FIG. 1, the endoscope 1 includes an insertion portion 2, an operation portion 3, and a cable 4. The insertion portion 2 is a long member that can be inserted into a subject. The operation portion 3 is contiguously provided on a proximal end side of the insertion portion 2. The cable 4 is a composite cable extending from the operation portion 3.

The insertion portion 2 includes a distal end portion 5, a bending portion 6, and a flexible tube portion 7, being a flexible tube. The distal end portion 5 is disposed at a distal end of the insertion portion 2. The bending portion 6 is actively bendable. The bending portion 6 is contiguously provided on a proximal end side of the distal end portion 5. The flexible tube portion 7 is contiguously provided on a proximal end side of the bending portion 6. The flexible tube portion 7 is connected in such a way as to extend from a distal end of the operation portion 3.

The operation portion 3 includes a first operation portion (first operation section) 10, a second operation portion (second operation section) 11, and a third operation portion 12, the first operation portion 10 being provided on a proximal end side of the operation portion 3, the second operation portion 11 being provided at an intermediate portion of the operation portion 3, the third operation portion 12 being provided on a distal end side of the operation portion 3. The operation portion 3 is formed such that two shells 3a, 3b, being exterior bodies made of synthetic resin or the like, are bonded to each other in a left and right direction by screws or the like. In other words, the two divided shells 3a, 3b are made to overlap with each other to form an exterior body of the operation portion 3.

The first operation portion 10 is provided with an angle lever 16, being an operating element. The angle lever 16 is an operation handle provided for operating bending of the bending portion 6 in an up and down direction. The first operation portion 10 may also be provided with another angle lever for operating bending of the bending portion 6 in the left and right direction.

The second operation portion 11 is a grasping portion to be grasped by a user. The second operation portion 11 includes a grip 13 formed into a concave-convex shape that allows the user to grasp the second operation portion 11 with fingers positioned along the grip 13.

A plurality of vent holes 21 are formed in each side surface of the first operation portion 10. A plurality of vent holes 22 are formed in each side surface of the second operation portion 11 at a lower portion. The plurality of vent holes 21, 22 are formed in each of two shells 3a, 3b. The plurality of vent holes provides a ventilation path from inside the housing to outside the housing. The plurality of vent holes is located in at least one of (i) the first operation section and (ii) a portion of the second operation section other than the grasping portion.

The plurality of vent holes 21, 22 are a plurality of hole portions provided for releasing heat in the operation portion 3 to outside. The second operation portion 11 may not have the plurality of vent holes 22 at a portion grasped by the user.

When the endoscope 1 is in a general use state in which the endoscope 1 is grasped by the user with the distal end side of the operation portion 3 being located on a lower side and with the proximal end side of the operation portion 3 being located on an upper side, for example, outside air is suctioned into the operation portion 3 from the plurality of vent holes 22, which are located on the lower side, and hot air in the operation portion 3 is discharged from the plurality of vent holes 21, which are located on the upper side. In other words, an updraft is generated in the operation portion 3, so that a flow of air is caused through the plurality of vent holes 21, 22. Therefore, heat is prevented from stagnating in the operation portion 3 and hence, cooling effect is improved.

Sheets having waterproof durability, moisture permeability and the like, such as Gore-Tex (registered trademark), may be provided on outer surfaces or inner surfaces of the shells 3a, 3b of the operation portion 3. With such a configuration, in a case in which the endoscope 1 is of a reusable type, it is possible to prevent intrusion of water into the operation portion 3 from outside, and it is possible to allow only air or sterilizing gas for reprocessing treatment to pass through the operation portion 3.

Bending prevention protectors 8, 9 are connected to the third operation portion 12 at a distal end position and on a rear surface side, the protectors 8, 9 being formed of elastic members. The insertion portion 2 extends from the protector 8, which is connected at the distal end side. The cable 4 extends from the protector 9, which is connected at the rear surface side. In other words, the protectors 8, 9 are members that prevent kink of the insertion portion 2 or the cable 4.

A T-shaped pipe 15 is provided on a front surface side of the third operation portion 12. The T-shaped pipe 15 is detachably mounted on an accessory port (not shown) provided in the third operation portion 12. The T-shaped pipe 15 has a treatment instrument insertion opening and a suction pipe sleeve. A forceps plug (not shown) is mounted on the treatment instrument insertion opening of the T-shaped pipe 15. Conduits (not shown), such as a treatment instrument insertion channel and a suction channel, that are disposed in the insertion portion 2 from the operation portion 3 are connected to the accessory port.

The operation portion 3 may have remote switches, an air/liquid feeding button, a suction button and the like (not shown). The remote switches are operation switches for a video system, pausing an image, recording, switching of photometry, image magnification, and the like being assigned to the respective switches. The air/liquid feeding button is an operation button that controls an action of feeding fluid from a fluid feeding portion (not shown) provided at the distal end portion 5 of the insertion portion 2. The suction button is an operation button that controls pressure in conduits (not shown), such as the treatment instrument insertion channel and the suction channel, to a negative pressure.

The cable 4 is a composite cable in which wiring of a power feeding system, an image pickup system and the like and a liquid feeding tube (also referred to as a "liquid feeding channel" or "conduit") 41, which will be described later, are disposed. The conduit is a flow path to supply the fluid to the inside of the subject. A connector (not shown) is connected to an extension end of the cable 4. The connector is connected to, for example, a video processor, being external equipment (not shown), or to an air/liquid feeding device, such as a pump.

The insertion portion 2 is connected to a pipe sleeve 46 which is fixed to the third operation portion 12 disposed on the distal end side of the operation portion 3. The distal end portion 5 of the insertion portion 2 has an observation window and an illumination window (not shown). The distal end portion 5 incorporates an image sensor (not shown), such as a CCD or a CMOS, that performs photoelectric conversion on photographing light incident on the image sensor from the observation window. Wiring of the image pickup system is disposed such that the wiring extending from the image sensor is inserted through the insertion portion 2, the operation portion 3 and the cable 4, and extends to the connector.

The distal end portion 5 irradiates an inside of the subject with illumination light through the illumination window. Illumination light is propagated through a light guide 34 disposed in the insertion portion and the operation portion 3, the light guide 34 being a light guide body, which will be described later. The light guide 34 is connected to a light source apparatus 30 disposed in the operation portion 3. In a case in which the endoscope 1 is a ureteroscope (video uretero-renoscope), the distal end portion 5 has a laser irradiation window. Laser beam is also propagated through the light guide 34.

Figure 2:
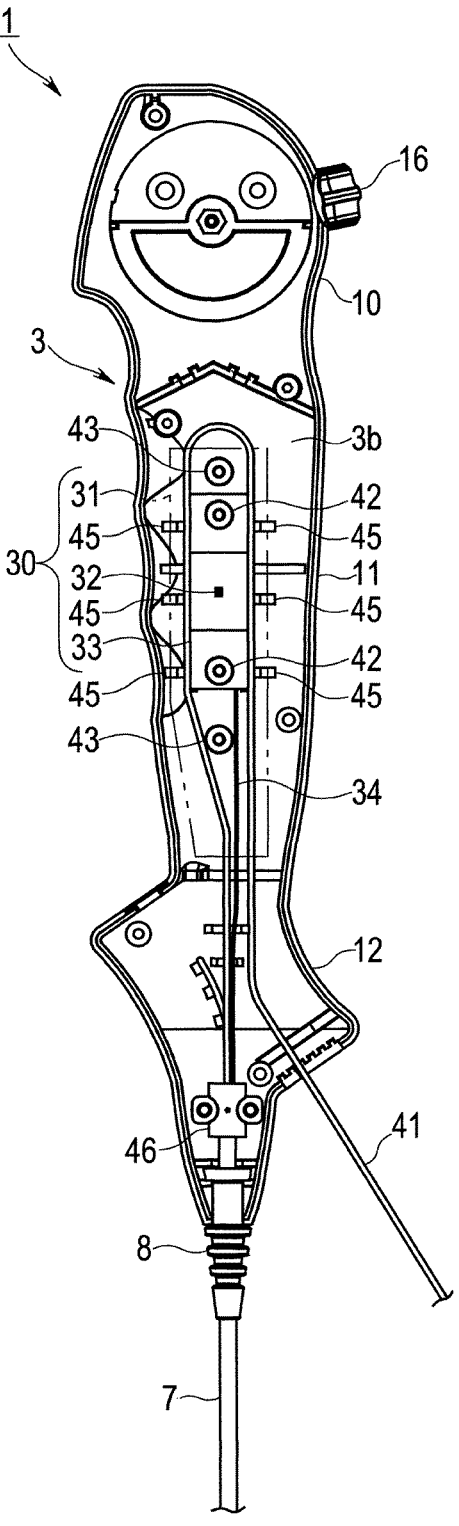
FIG. 2 is a plan view showing an inside of an operation portion of the endoscope.
Figure 3:
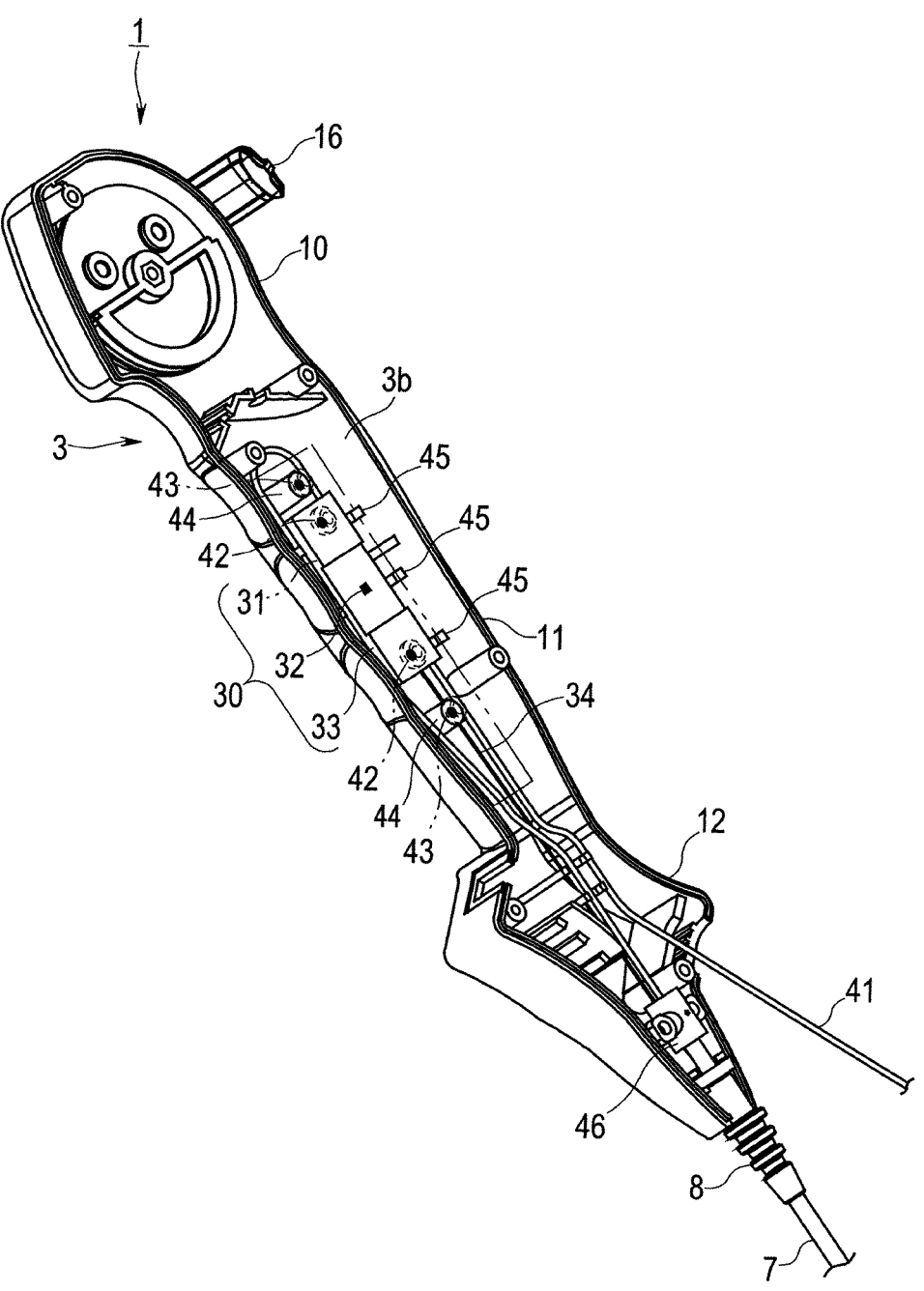
FIG. 3 is a perspective view showing the inside of the operation portion of the endoscope as viewed from a right side.
Figure 4:
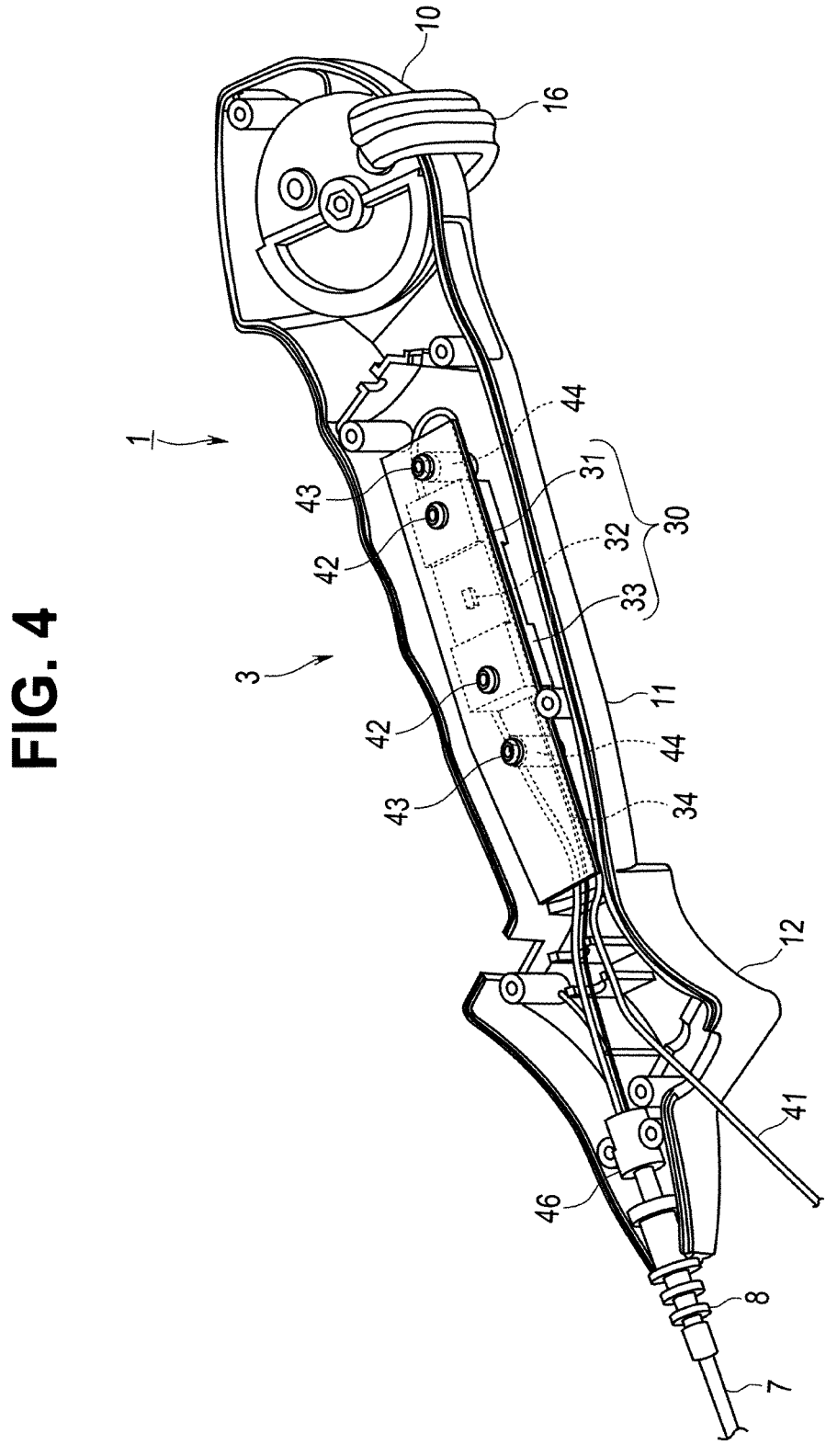
FIG. 4 is a perspective view showing the inside of the operation portion of the endoscope as viewed from a left side.

As shown in FIG. 2 to FIG. 4, the light source apparatus 30 is mounted in the operation portion 3 of the endoscope 1. The light source apparatus 30 is disposed at a position of the second operation portion 11 of the operation portion 3. In the present embodiment, the light source apparatus 30 is fixed to one shell 3b of the two shells 3a, 3b forming the exterior body of the operation portion 3. That is, the two shells 3a, 3b can form a housing of the operation portion 3.

Figure 5:
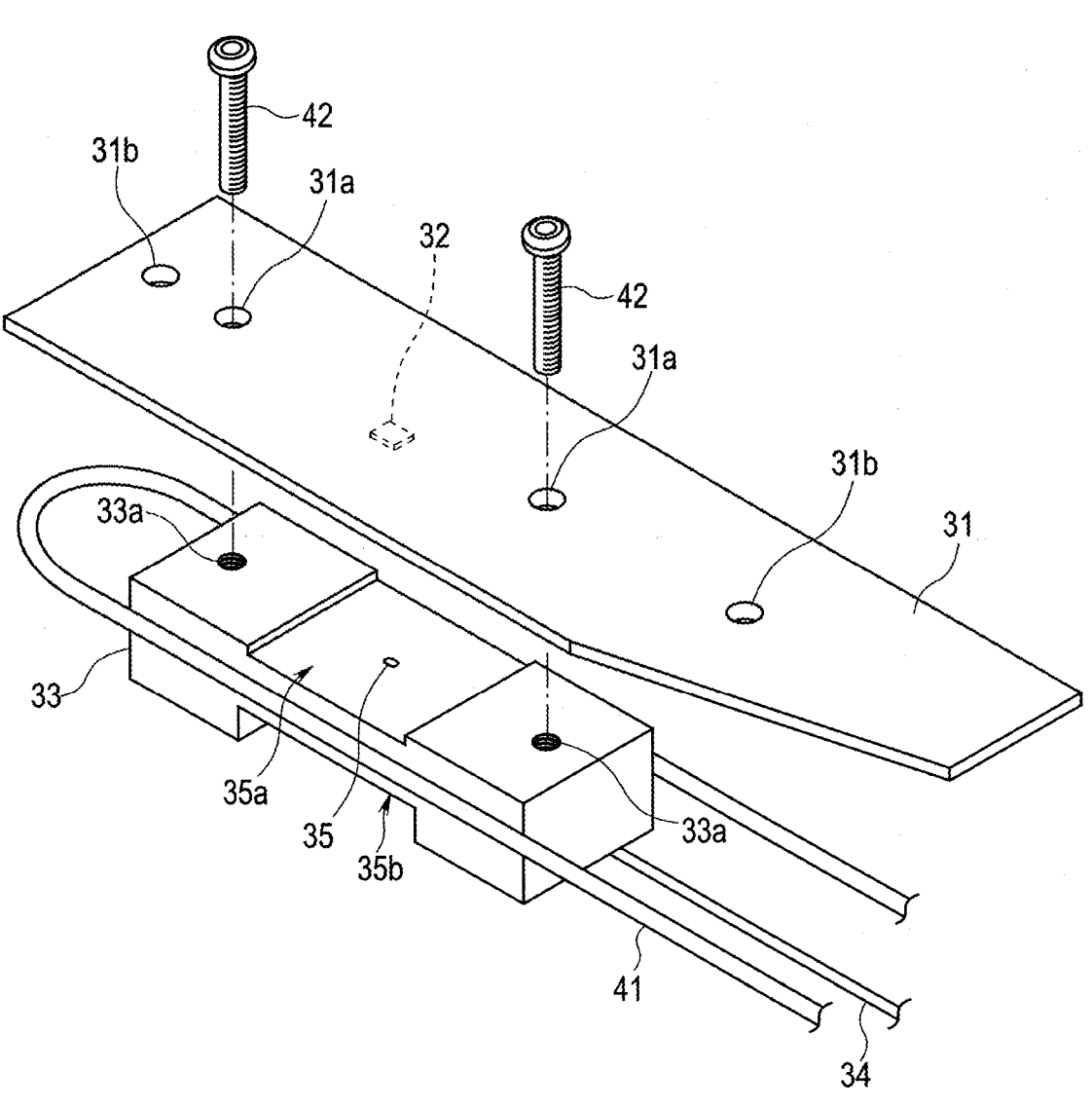
FIG. 5 is an exploded perspective view showing a light source apparatus with which a liquid feeding tube is in contact.
Figure 6:
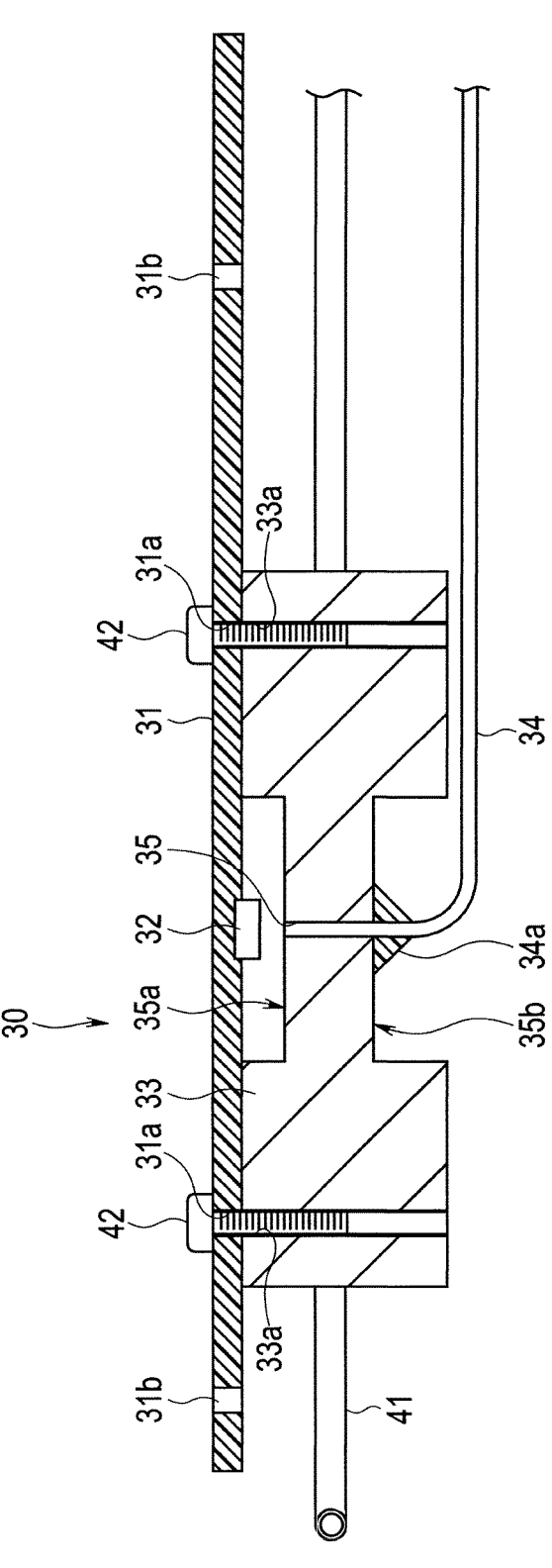
FIG. 6 is a cross-sectional view showing the light source apparatus with which the liquid feeding tube is in contact.

As shown in FIG. 5 and FIG. 6, the light source apparatus 30 includes a substrate (fixture) 31, a light emitting diode (LED or light emission body) 32, a fiber fixation block (fixture) 33, and the light guide 34, being the light guide body that transmits light. The substrate 31 and the fiber fixation block 33 form a fixation member (fixture) that holds the LED 32. The light guide 34 transmits light from the light emission body 32 to a light emission window of the insertion portion 2. A proximal end portion of the light guide can be attached to the fixture. The light emission body 32 and the light guide 34 may be attached to the fixture with the light emission body 32 facing the proximal end of the light guide 34. A portion of the fixture may be a heat sink to absorb heat generated from the light emission body 32.

The substrate 31 is a laminated substrate including wiring metal, an insulating thin film, and the like. The substrate 31 has four screw holes 31a, 31b in total. LED driving wiring (not shown) is connected to the substrate 31. The LED driving wiring is disposed in such a way as to be inserted through the cable 4 from the operation portion 3, and to extend to the connector.

At least one LED 32 is mounted on the substrate 31, the LED 32 being a light emission body that forms a light source. In other words, the LED 32 is attached to the substrate 31. In a case in which the endoscope 1 is an ureteroscope (video uretero-renoscope), the light source apparatus 30 is configured to include a semiconductor laser, being the light emission body, as the light source.

The fiber fixation block 33, being the fixation member, is a massive rectangular block member made of metal, such as aluminum. The fiber fixation block 33 has recessed portions 35a, 35b on both surfaces in the up and down direction when viewing a paper surface, each of the recessed portions 35a, 35b being formed at a center portion of the surfaces.

The fiber fixation block 33 has two screw holes 33a that fix the substrate 31 with fixing screws 42. The fixing screws 42 are caused to pass through the screw holes 31a of the substrate 31. The fixing screws 42 are threadedly fitted in the screw holes 33a of the fiber fixation block 33. With such a configuration, the substrate 31 is fixed to the fiber fixation block 33 at two positions with the two fixing screws 42.

The fiber fixation block 33 has a fiber installation hole 35. The fiber installation hole 35 is formed in such a way as to penetrate through the recessed portions 35a, 35b of the fiber fixation block 33 at a center.

A rear end portion of the light guide 34, being at least one optical fiber, is inserted into the fiber installation hole 35. The light guide 34 may be of a bundle type in which a plurality of optical fibers is bundled.

The light guide 34 is fixed to the fiber fixation block 33 by an adhesive agent 34a (see FIG. 6) on a recessed portion 35b side of the fiber fixation block 33, which is a lower portion side when viewing the paper surface. In this state, a position of an end surface of the light guide 34 is aligned with a position of a surface of the recessed portion 35a of the fiber fixation block 33.

The LED 32 is disposed to face the end surface of the light guide 34 in a state in which the substrate 31 is fixed to the fiber fixation block 33. An optical system, such as a lens, may be provided in the fiber installation hole 35 of the fiber fixation block 33.

In the light source apparatus 30 having the above-mentioned configuration, a fixing screw 43 is caused to pass through each of the two screw holes 31b of the substrate 31. The fixing screws 43 are threadedly fitted in cylindrical screw receivers 44 provided in the shell 3b of the operation portion 3 (see FIG. 3 and FIG. 4).

Figure 7:
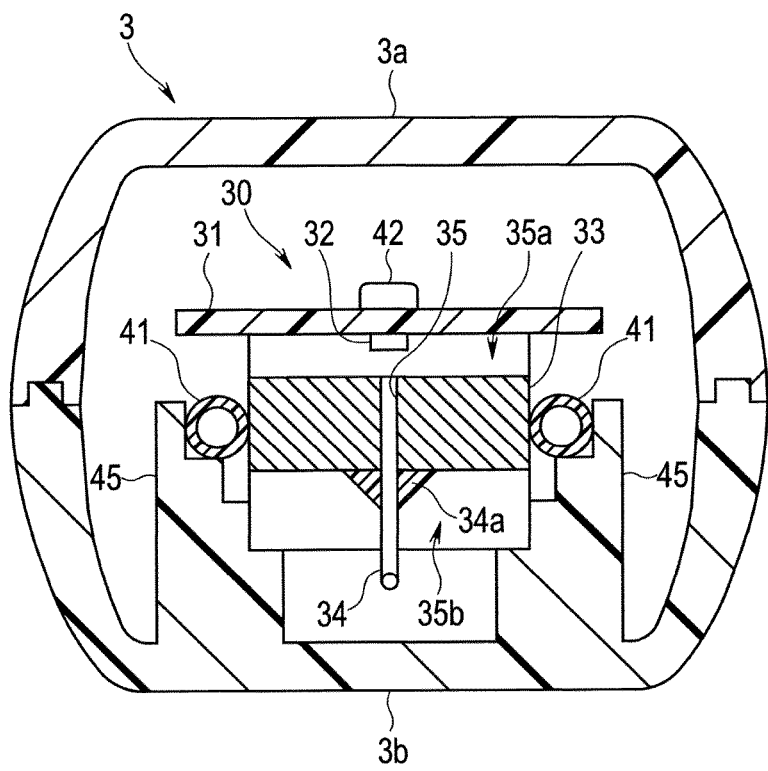
FIG. 7 is a cross-sectional view showing the operation portion provided with the light source apparatus with which the liquid feeding tube is in contact.

With such a configuration, the light source apparatus 30 is fixed to the shell 3b of the operation portion 3 at two positions with the two fixing screws 43. In this state, as shown in FIG. 7, the light source apparatus 30 is held in a state of engaging with a plurality of ribs 45. The plurality of ribs (a surface of the exterior body) 45 protrude from the shell 3b of the operation portion 3, and is formed into a step shape. The plurality of ribs 45 has a seating surface.

The plurality of ribs 45 having a step shape are formed at positions that face side surfaces of the fiber fixation block 33. With such a configuration, the light source apparatus 30 is held by the plurality of ribs 45. In the present embodiment, the plurality of ribs 45 including three ribs 45 on one side, that is, six ribs 45 in total on both sides, are provided.

The fiber fixation block 33 of the light source apparatus 30 also serves as a heat absorbing member that absorbs heat of the LED 32, being a heat source of a heat generating member. In other words, the fiber fixation block 33 is in contact with the substrate 31 to which heat of the LED 32 is transferred, and the fiber fixation block 33 absorbs the heat. The fiber fixation block 33 also has an effect of absorbing heat around the LED 32, thus reducing an atmospheric temperature of the LED 32.

In the operation portion 3 of the endoscope 1, a conduit is formed by a liquid feeding tube 41. The conduit includes a first portion and a second portion. The first portion is located outside the exterior body. The second portion is located inside the exterior body and disposed in such a way as to lie along and to be in close contact with the side surfaces of the fiber fixation block 33 of the light source apparatus 30.

The liquid feeding tube 41 is turned on a proximal end side of the operation portion 3 in such a way as to surround the fiber fixation block 33 of the light source apparatus 30, and then extends toward the distal end side. The liquid feeding tube 41 is disposed in such a way as to be inserted in through the insertion portion 2 and to extend to the fluid feeding portion (not shown) of the distal end portion 5.

For the liquid feeding tube 41, a soft bendable conduit made of PTFE (polytetrafluoroethylene) or PVC (polyvinyl chloride) is used.

The liquid feeding tube 41 is held such that the liquid feeding tube 41 is fitted in stepped portions of the plurality of ribs 45 of the shell 3b of the operation portion 3 and an outer surface of the liquid feeding tube 41 is in close contact with both side surfaces of the fiber fixation block 33. When liquid is fed, the liquid feeding tube 41 absorbs heat from the fiber fixation block 33, thus cooling the fiber fixation block 33.

The outer surface of the liquid feeding tube 41 may be in contact with the fiber fixation block 33 at least at one point or one part, or at a plurality of portions. The liquid feeding tube 41 may be wound around the fiber fixation block 33 such that the outer surface of the liquid feeding tube 41 is in contact with the plurality of side surfaces of the fiber fixation block 33.

As described above, the endoscope 1 of the present embodiment is configured such that the light source apparatus 30 is mounted in the operation portion 3. In the endoscope 1, the LED 32 is used as the light emission body, being the light source of the light source apparatus 30. In the light source apparatus 30, the LED 32 forms the heat source. The light source apparatus 30 includes the fiber fixation block 33 that absorbs heat of the LED 32.

Further, in the endoscope 1, the liquid feeding tube 41 is disposed in such a way as to lie along and to be in contact with the fiber fixation block 33. With such a configuration, in the endoscope 1, heat from the fiber fixation block 33 is absorbed by fluid, such as water or saline flowing through the liquid feeding tube 41 when the liquid is fed. Accordingly, the fiber fixation block 33 is cooled.

As described above, in the endoscope 1, liquid is fed with the liquid feeding tube 41 being in close contact with the fiber fixation block 33 to cool the fiber fixation block 33 by absorbing heat of the LED 32, the fiber fixation block 33 fixing the light guide 34 and being provided in the vicinity of the LED 32.

In a case in which the endoscope 1 is configured to have a perfusion function of performing liquid feeding and liquid suction simultaneously, for example, in a case in which the endoscope 1 is a video uretero-renoscope, it is possible to use the liquid feeding tube 41 that is originally included as a conventional functional component of the endoscope. Therefore, the endoscope 1 does not require a new cooling tube for cooling heat of the LED 32, being a heat generating component provided in the operation portion 3, thus requiring no additional cost. Accordingly, the endoscope 1 can achieve a low-cost configuration.

In other words, by using the liquid feeding tube 41 that is conventionally included in the endoscope 1, the endoscope 1 has a structure having a liquid cooling function. Therefore, the endoscope 1 has a structure that can cool the heat generating component in the operation portion 3 at a low cost without requiring a new cooling source. Further, the endoscope 1 has a structure in which the liquid feeding tube 41 is caused to only lie in the operation portion 3 and hence, the endoscope 1 can be easily assembled.

Fluid flowing through the liquid feeding tube 41 absorbs heat of the LED 32 through the fiber fixation block 33, thus being heated and hence, viscosity of the fluid reduces. With such a configuration, even when the liquid feeding tube 41 has a small diameter, friction of fluid with the conduit is reduced and hence, a pressure loss of flowing liquid is reduced. In other words, in the endoscope 1, a pressure load on a liquid feeding source and a whole conduit is reduced. With such a configuration, a system of the endoscope 1 can also obtain a secondary effect that a risk of damage, failure, or the like is reduced.

As described above, the endoscope 1, being the insertion instrument of the present embodiment, can prevent a temperature rise of the light source apparatus 30 mounted in the operation portion 3, particularly, a temperature rises of the LED 32 or a light source of a semiconductor laser. With such a configuration, it becomes unnecessary for the endoscope 1 to unavoidably reduce brightness of illumination light or to unavoidably reduce intensity of laser beam for a purpose of preventing a temperature rise.

Further, it becomes unnecessary for a user, such as a doctor, to use the endoscope 1 in a state in which a temperature in a use environment (room temperature or the like) is reduced to prevent a temperature rise of the light source apparatus 30 mounted in the operation portion 3 of the endoscope 1.

Accordingly, the endoscope 1 of the present embodiment is configured to have a structure that can cool the heat generating component in the operation portion 3 at a low cost by using a functional structure that the endoscope 1 originally has.

First Modification

Figure 8:
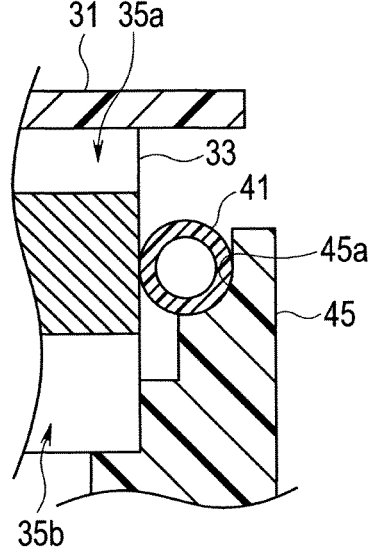
FIG. 8 is a partial cross-sectional view showing a rib holding a light source apparatus of a first modification and having a curved surface that is in contact with the liquid feeding tube.

In the present modification, as shown in FIG. 8, each of a plurality of ribs 45 has a curved surface 45*a* having an arc shape similar to a shape of a portion of an outer shape of the liquid feeding tube 41. The curved surfaces 45*a* of the plurality of ribs 45 are formed at positions that face the fiber fixation block 33. The liquid feeding tube 41 is held in a state of engaging with recessed portions of the plurality of ribs 45, each recessed portion having the curved surface 45*a*.

With such a configuration, a contact area of the liquid feeding tube 41 with the plurality of ribs 45 increases. Therefore, heat from the fiber fixation block 33 is transferred to the plurality of ribs 45 through the liquid feeding tube 41. The heat transferred to the plurality of ribs 45 is dispersed into the shell 3*b* of the operation portion 3. Accordingly, efficiency of cooling the fiber fixation block 33 is improved.

Second Modification

Figure 9:
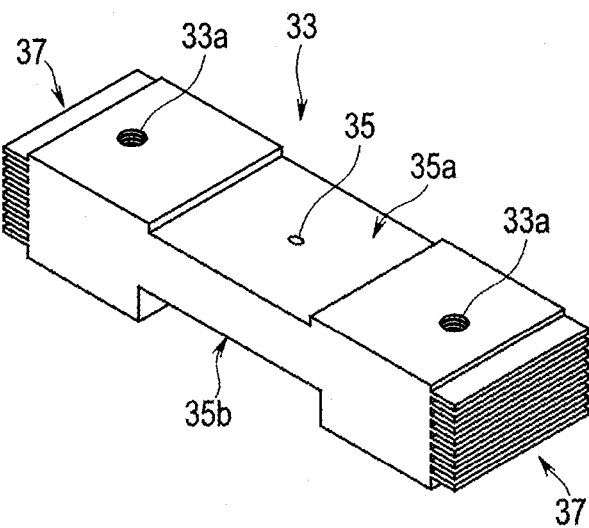
FIG. 9 is a perspective view showing a fiber fixation block of a second modification.

As shown in FIG. 9, a fiber fixation block 33 of the present modification may be configured such that a plurality of heat radiating fins 37, being heat radiating members, are integrally formed to improve cooling performance.

Third Modification

Figure 10:
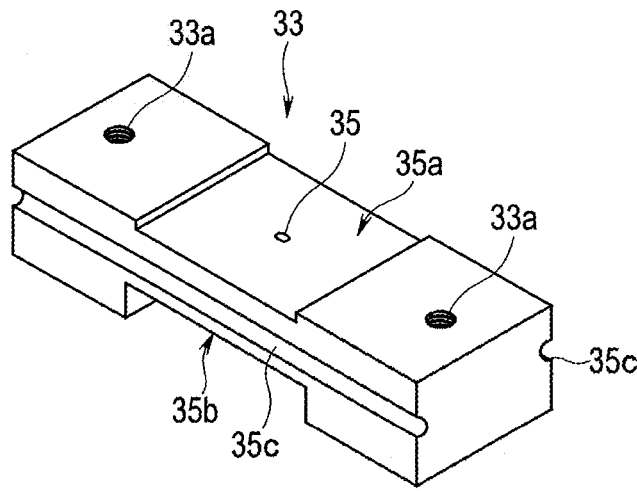
FIG. 10 is a perspective view showing a fiber fixation block of a third modification.
Figure 11:
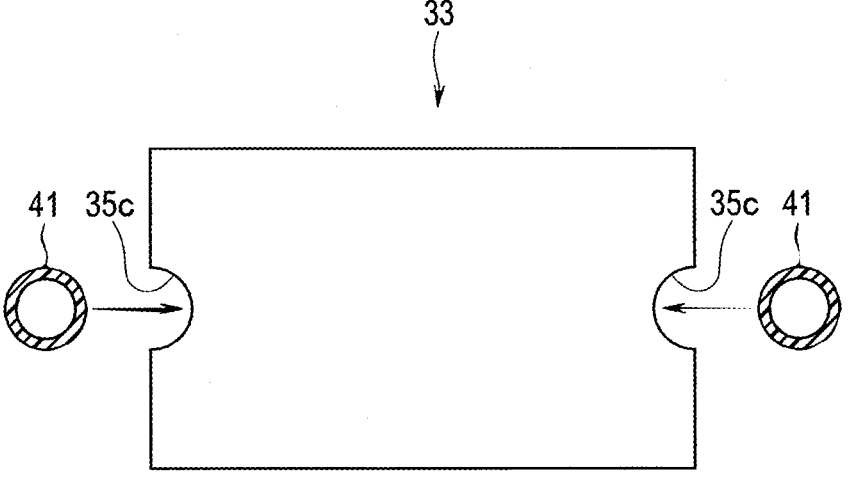
FIG. 11 is a diagram showing the fiber fixation block of the third modification with which the liquid feeding tube is to be in contact.
Figure 12:
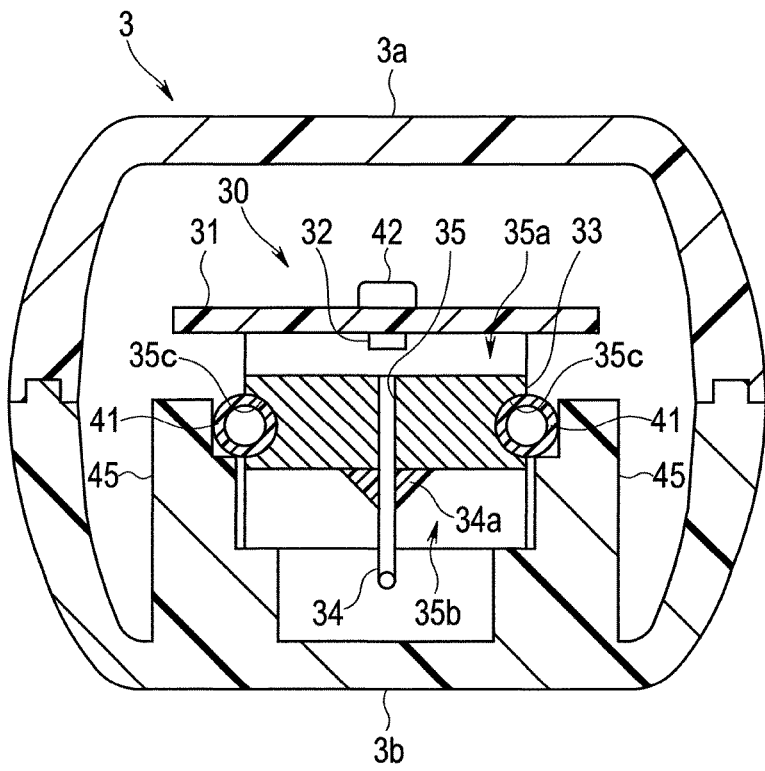
FIG. 12 is a cross-sectional view showing an operation portion provided with a light source apparatus of the third modification with which the liquid feeding tube is in contact.

As shown in FIG. 10 to FIG. 12, a fiber fixation block 33 of the present modification has recessed grooves (groove) 35*c* on both side surfaces, the recessed grooves 35*c* being holding portions each of which is formed of a round groove extending in a longitudinal direction. The two recessed grooves 35*c* are formed on two side surfaces of the fiber fixation block 33 with which the liquid feeding tube 41 is in contact, and each of the two recessed grooves 35*c* has a curved surface having an arc shape similar to a shape of a portion of an outer shape of the liquid feeding tube 41. Each of the two recessed grooves 35*c* is set to have a cross-sectional shape with a radius equal to or less than a radius of an outer circular shape of the liquid feeding tube 41.

The liquid feeding tube 41 is held such that a part of the liquid feeding tube 41 is covered by and is seated in the recessed grooves 35*c* of the fiber fixation block 33. With such a configuration, a contact area of the liquid feeding tube

41 with the fiber fixation block 33 increases. Therefore, the liquid feeding tube 41 can easily absorb heat from the fiber fixation block 33.

Accordingly, efficiency of cooling the fiber fixation block 33 is improved. Further, it is possible to easily assemble components when the liquid feeding tube 41 is caused to lie along the fiber fixation block 33.

Figure 13:
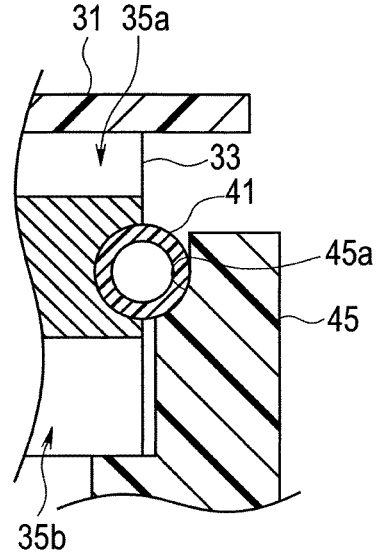
FIG. 13 is a partial cross-sectional view showing a rib holding the light source apparatus of the third modification and having a curved surface that is in contact with the liquid feeding tube.

As a configuration similar to the configuration of the above-mentioned first modification, as shown in FIG. 13, each of the plurality of ribs 45 may have the curved surface 45*a* at a position that faces the fiber fixation block 33, the curved surface 45*a* having the arc shape similar to the shape of the portion of the outer shape of the liquid feeding tube 41.

Fourth Modification

Figure 14:
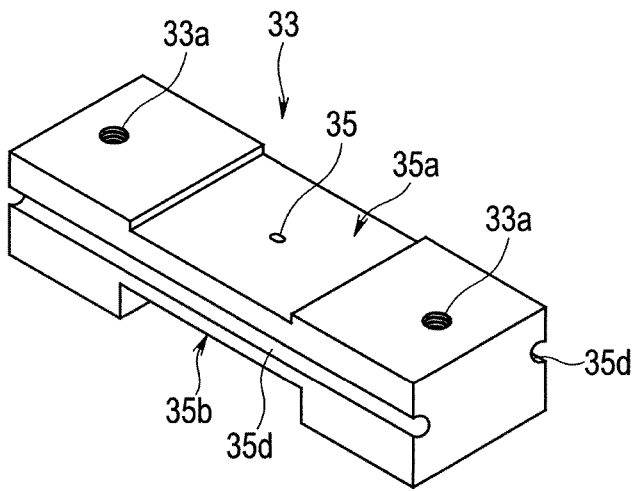
FIG. 14 is a perspective view showing a fiber fixation block of a fourth modification having recessed grooves.
Figure 15:
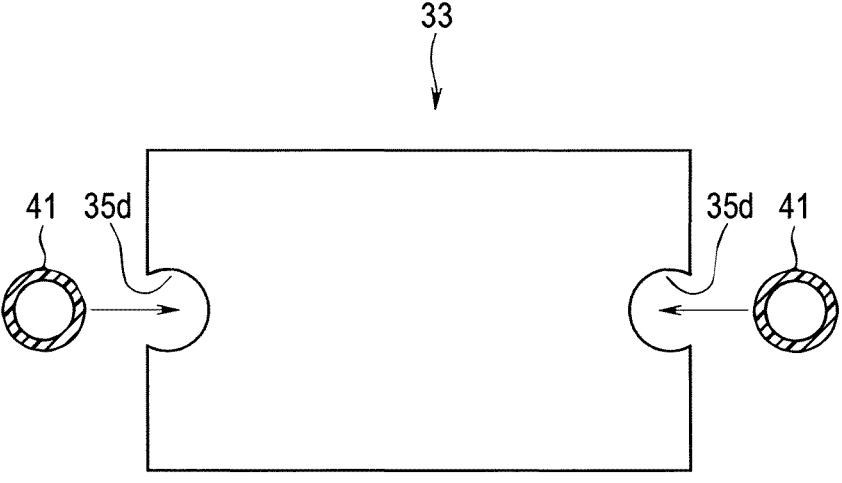
FIG. 15 is a diagram showing the fiber fixation block of the fourth modification with which the liquid feeding tube is to be in contact.
Figure 16:
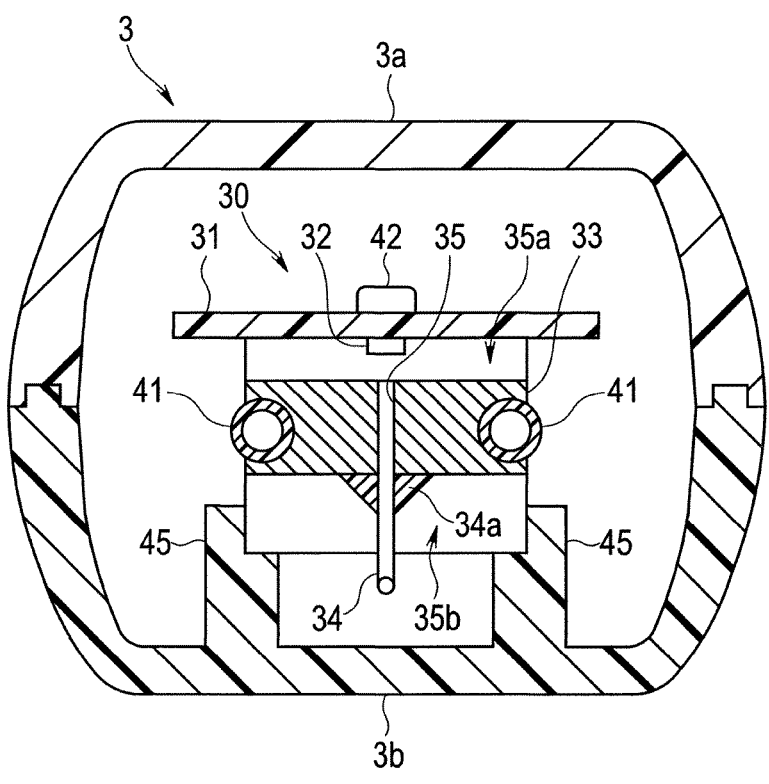
FIG. 16 is a cross-sectional view showing an operation portion provided with a light source apparatus of the fourth modification with which the liquid feeding tube is in contact.

As a configuration similar to the configuration of the above-mentioned third modification, as shown in FIG. 14 to FIG. 16, a fiber fixation block 33 of the present modification has recessed grooves 35*d* on both side surfaces, the recessed grooves 35*d* being holding portions each of which is formed of a round groove extending in the longitudinal direction. In the present modification, each of the two recessed grooves 35*d* is set to have a cross-sectional shape with a radius larger than a radius of an outer circular shape of the liquid feeding tube 41.

The liquid feeding tube 41 is held such that a part of the liquid feeding tube 41 is covered by and fitted in the recessed grooves 35*d* of the fiber fixation block 33. In other words, a so-called snap fit structure is formed by the liquid feeding tube 41 and the recessed grooves 35*d* of the fiber fixation block 33. The liquid feeding tube 41 is held in a state of being fitted in the recessed grooves 35*d* of the fiber fixation block 33.

Even when such a configuration is adopted, a contact area of the liquid feeding tube 41 with the fiber fixation block 33 increases and hence, in the same manner as the above-mentioned third modification, efficiency of cooling the fiber fixation block 33 is improved. In addition to the above, components can be easily assembled by fitting the liquid feeding tube 41 into the recessed grooves 35*d* of the fiber fixation block 33. Moreover, it becomes unnecessary to adopt the structure in which the liquid feeding tube 41 is held by the plurality of ribs 45.

Fifth Modification

Figure 17:
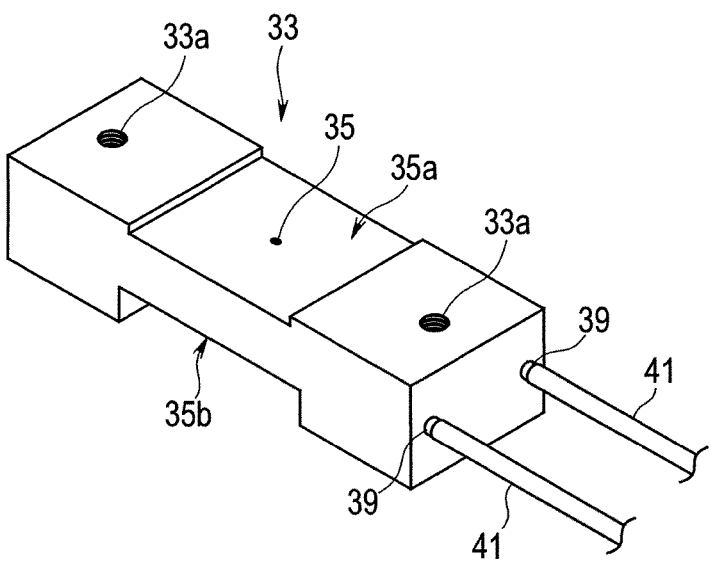
FIG. 17 is a perspective view showing a fiber fixation block of a fifth modification to which liquid feeding tubes are connected.
Figure 18:
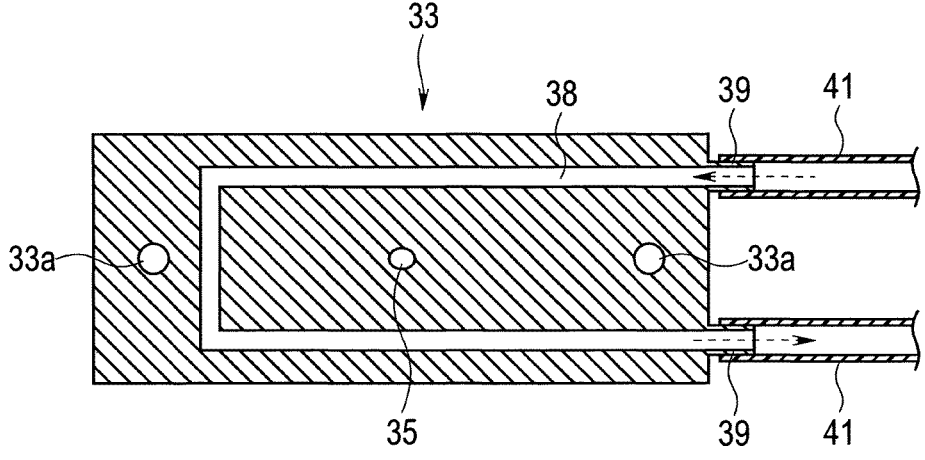
FIG. 18 is a cross-sectional view showing the fiber fixation block of the fifth modification to which the liquid feeding tubes are connected and which has a flow passage.
Figure 19:
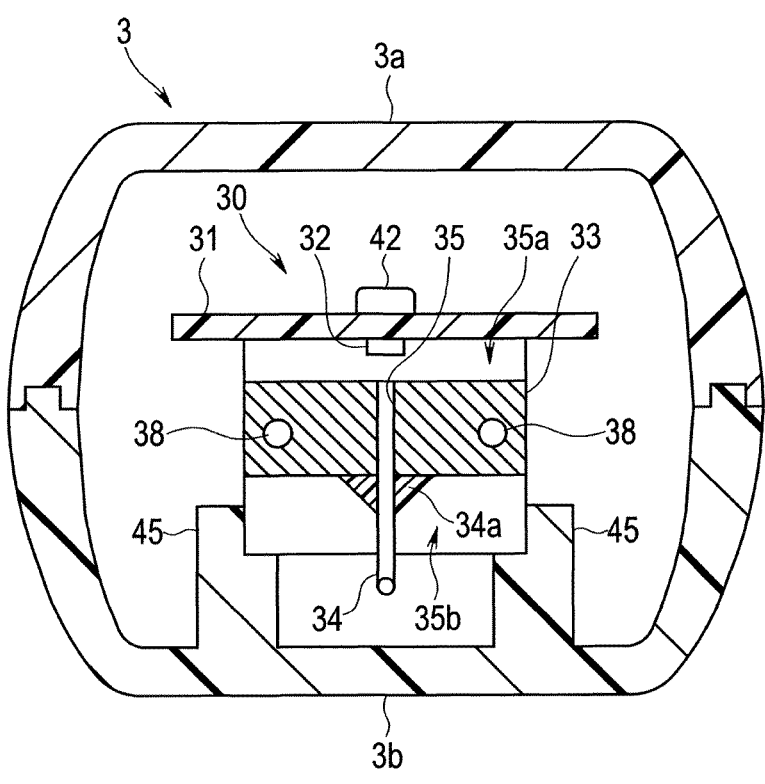
FIG. 19 is a cross-sectional view showing an operation portion provided with a light source apparatus of the fifth modification having the flow passage.

As shown in FIG. 17 to FIG. 19, the conduit of the present modification includes a first portion, a second portion and a third portion. The first portion is located outside the exterior body. The second portion is a flow passage 38 that is formed in a fiber fixation block 33 of the present modification. The third portion is located inside the exterior body and between the first portion and the second portion. The fiber fixation block 33 includes two connecting portions 39 to which liquid feeding tubes (third portion) 41 are connected. When the liquid feeding tubes 41 are connected to the two connecting portions 39, the liquid feeding tubes 41 communicate with the flow passage 38. In other words, when the second portion is connected to the two connecting portions 39, the second portion communicate with the third portion. In the present modification, two liquid feeding tubes 41 are provided, that is, the liquid feeding tube 41 extending toward the cable 4 and the liquid feeding tube 41 extending toward the insertion portion 2.

In the fiber fixation block 33 having such a configuration, a fluid supplied from the liquid feeding tube 41 flows through the flow passage 38 formed in the fiber fixation block 33. The fiber fixation block 33 is cooled by the fluid flowing through the flow passage 38 formed in the fiber fixation block 33.

In other words, the fiber fixation block 33 has a structure in which the fiber fixation block 33 is directly cooled by the fluid flowing through the fixation block 33 instead of being cooled through the liquid feeding tube 41. Therefore, efficiency of cooling the fiber fixation block 33 is improved.

Further, it is unnecessary to dispose the liquid feeding tube 41 in such a way as to lie in the operation portion 3. Therefore, there is no possibility of bending or kink of the liquid feeding tube 41. Accordingly, it is possible to form the liquid feeding tube 41 from a small-diameter tube body having a smaller wall thickness. As a result, this contributes to a reduction in a diameter of the insertion portion 2 through which the liquid feeding tube 41 is inserted.

Figure 20:
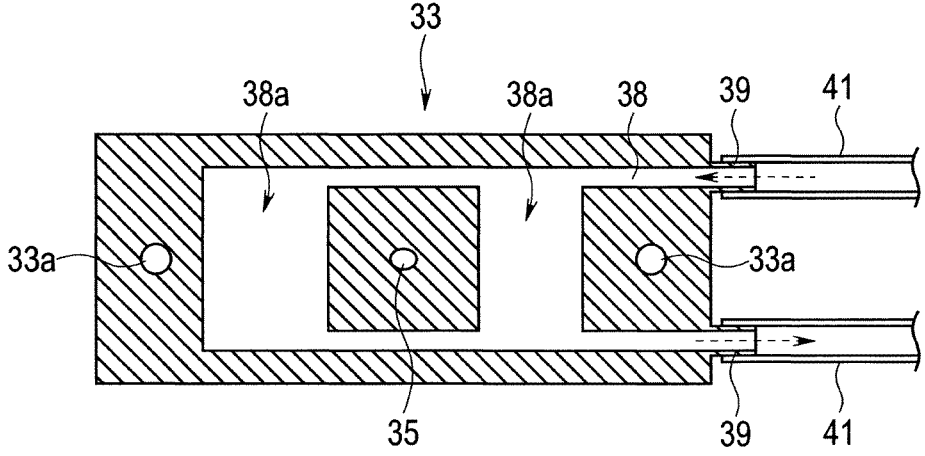
FIG. 20 is a perspective view showing the fiber fixation block of the fifth modification in a state in which the liquid feeding tubes are connected to the fiber fixation block and the fiber fixation block has space portions communicating with the flow passage.
Figure 21:
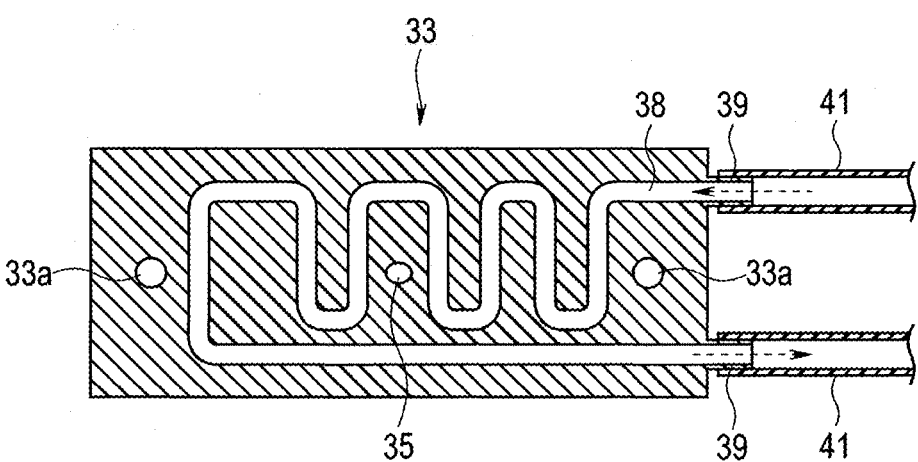
FIG. 21 is a perspective view showing the fiber fixation block of the fifth modification in a state in which the liquid feeding tubes are connected to the fiber fixation block and the flow passage meanders.
Figure 22:
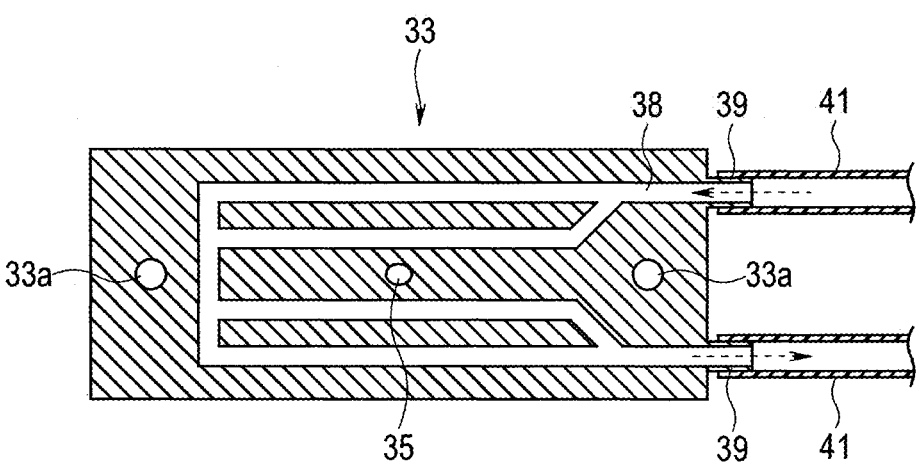
FIG. 22 is a perspective view showing the fiber fixation block of the fifth modification in a state in which the liquid feeding tubes are connected to the fiber fixation block and the flow passage branches.

As shown in FIG. 20, the fiber fixation block 33 may have space portions 38a communicating with the flow passage 38 formed in the fiber fixation block 33. The flow passage 38 may meander as shown in FIG. 21, or may branch as shown in FIG. 22.

Sixth Modification

Figure 23:
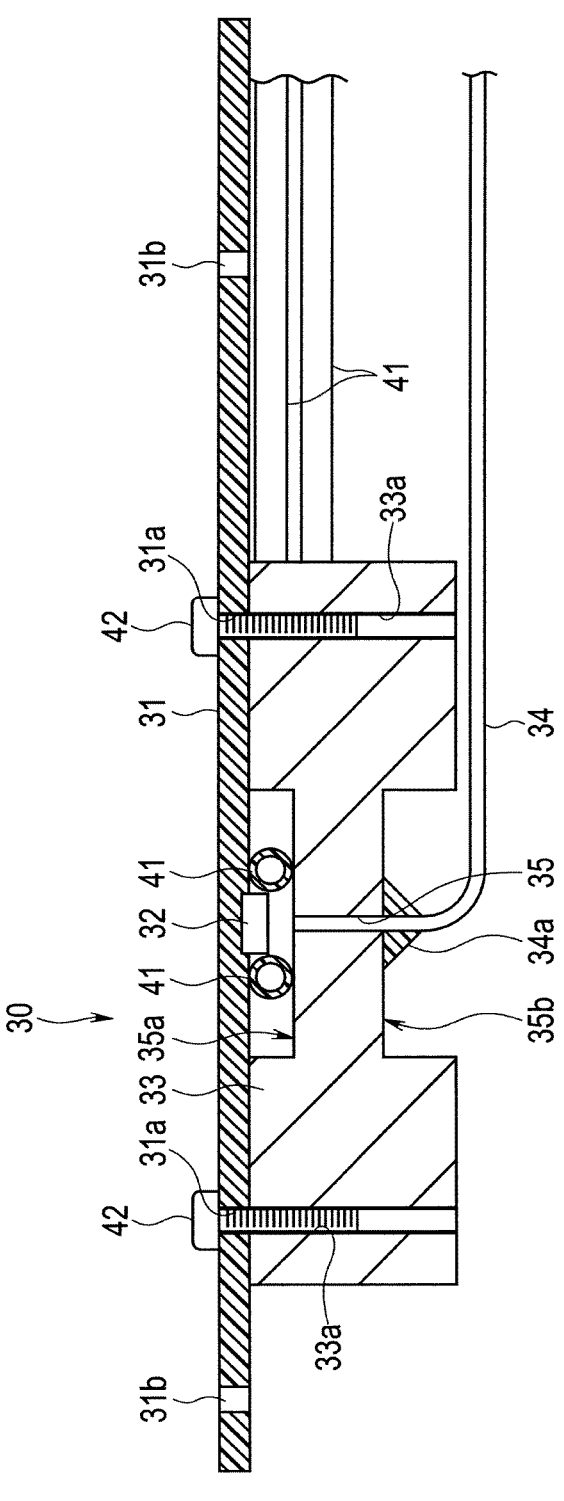
FIG. 23 is a cross-sectional view showing a light source apparatus of a sixth modification in which the liquid feeding tube is in contact with an LED.

In the present modification, as shown in FIG. 23, the liquid feeding tube 41 is not configured to be in contact with the fiber fixation block 33, but is provided in such a way as to be in contact with the LED 32. In the present modification, the liquid feeding tube 41 is disposed between the substrate 31 and the fiber fixation block 33 in a state of being inserted through the recessed portion 35a of the fiber fixation block 33. The liquid feeding tube 41 is first caused to pass through the recessed portion 35a of the fiber fixation block 33, is turned, and is then caused to pass through the recessed portion again.

The LED 32, being a heat generating source, is directly cooled by a fluid flowing through the liquid feeding tube 41 that is in contact with the LED 32. The LED 32 is directly cooled as described above, so that efficiency of cooling the LED 32 is improved and hence, deterioration of the LED 32 caused by heat can be prevented.

Seventh Modification

Figure 24:
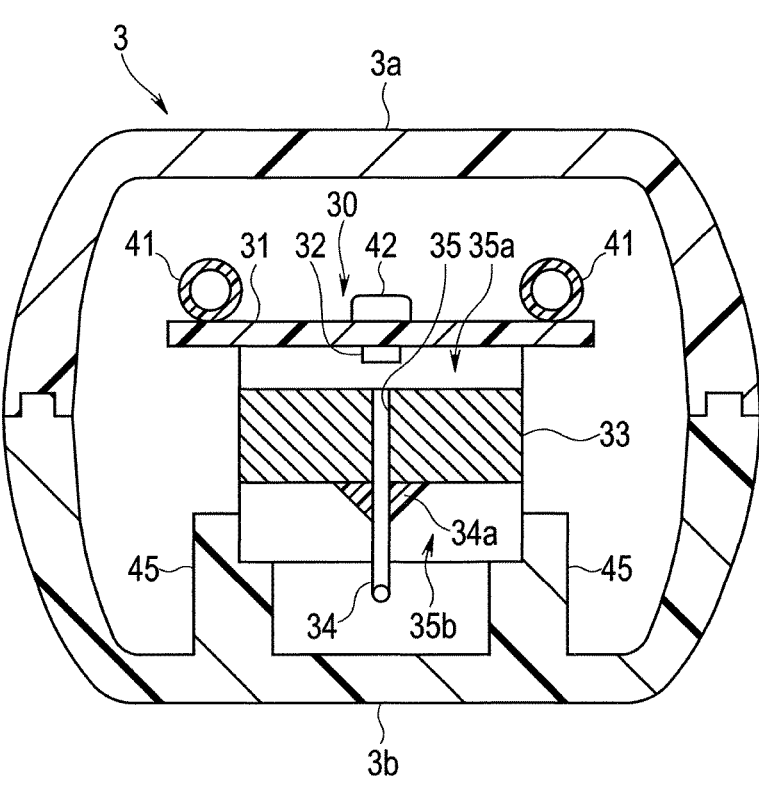
FIG. 24 is a cross-sectional view showing an operation portion provided with a light source apparatus of a seventh modification in which the liquid feeding tube is in contact with a substrate.

In the present modification, as shown in FIG. 24, the liquid feeding tube 41 is not configured to be in contact with the fiber fixation block 33, but is provided in such a way as to be in contact with a surface of the substrate 31. In the present modification, the liquid feeding tube 41 allows a fluid to flow through the liquid feeding tube 41, thus directly cooling the substrate 31 that is in contact with the liquid feeding tube 41.

Eighth Modification

Figure 25:
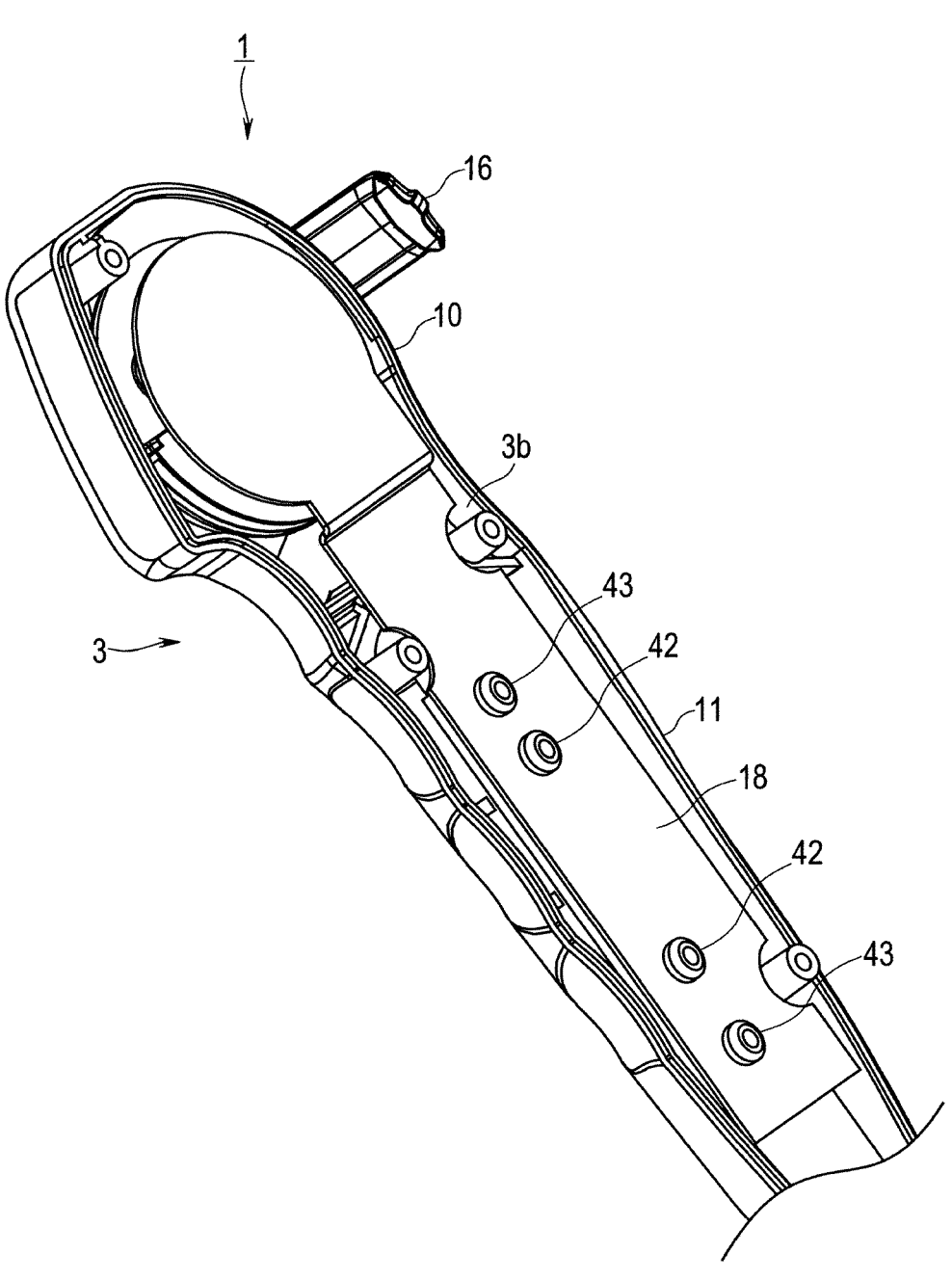
FIG. 25 is a perspective view, as viewed from a right side, partially showing an inside of an operation portion of an endoscope of an eighth modification, the operation portion being provided with a base plate.
Figure 26:
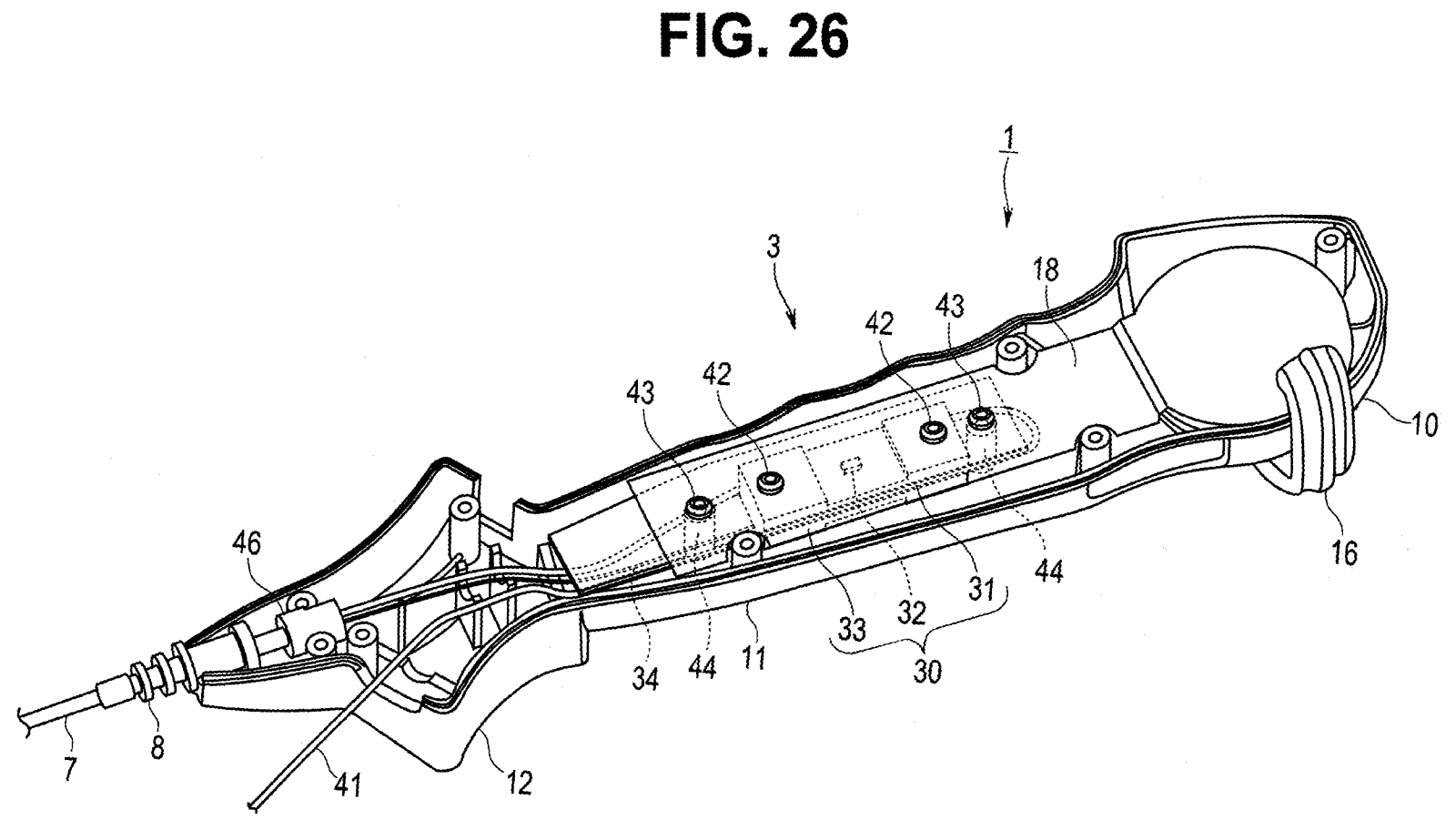
Figure 27:
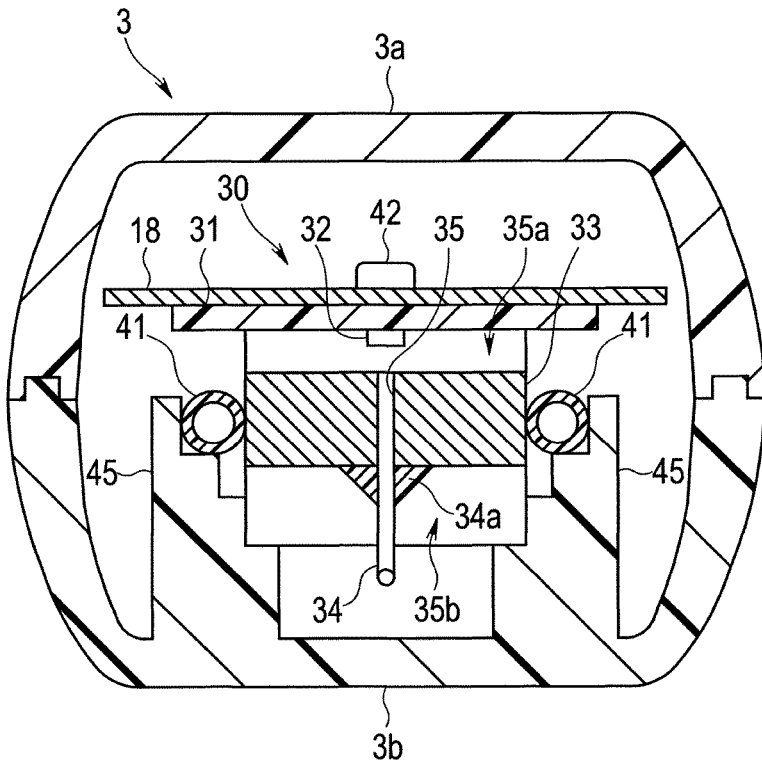
FIG. 27 is a cross-sectional view showing the operation portion of the eighth modification, the operation portion being provided with the base plate and a light source apparatus with which the liquid feeding tube is in contact.

As shown in FIG. 25 to FIG. 27, in an endoscope 1 of the present modification, a base plate 18, being a separate frame plate, is stacked on the substrate 31 of the light source apparatus 30 mounted in the operation portion 3. The base plate 18 forms a heat sink, being a heat radiating member formed from a metal plate, thus improving heat radiation effect of the LED 32, being the heat source of the light source apparatus 30.

Figure 28:
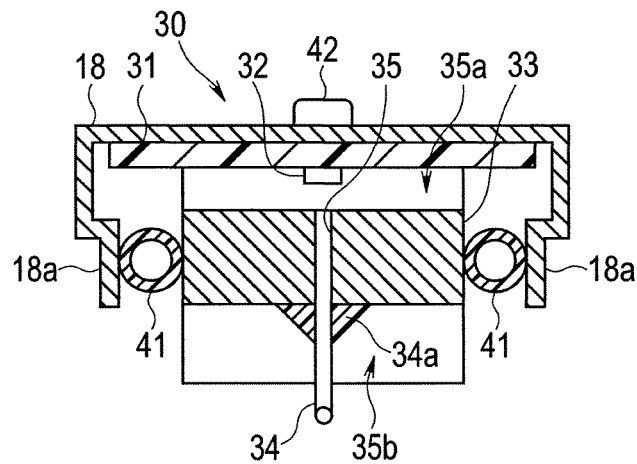
FIG. 28 is a cross-sectional view showing a state of the base plate and the light source apparatus in the eighth modification, the base plate including side portions each of which is in contact with the liquid feeding tube.

As shown in FIG. 28, the base plate 18 may include side portions 18a that are bent in such a way as to be in contact with the liquid feeding tube 41. The liquid feeding tube 41 is in contact with the side portions 18a of the base plate 18 and hence, efficiency of cooling the LED 32 is further improved.

Figure 29:
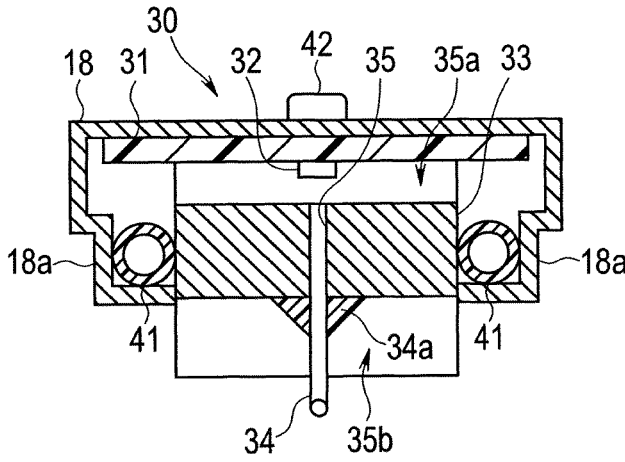
FIG. 29 is a cross-sectional view showing a state of the base plate and the light source apparatus in the eighth modification, the base plate including the side portions each of which is in contact with the liquid feeding tube in such a way as to surround the liquid feeding tube.
Figure 30:
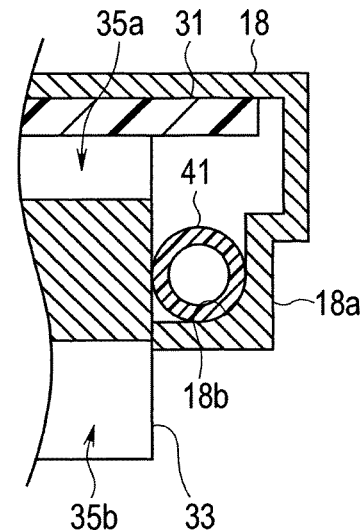
FIG. 30 is a partial cross-sectional view showing the base plate in the eighth modification including the side portions each of which has a curved surface that is in contact with the liquid feeding tube.

Side portions 18a of the base plate 18 may be bent in such a way as to surround the liquid feeding tube 41 as shown in FIG. 29. To increase a contact area with the liquid feeding tube 41, each of the side portions 18a of the base plate 18 may also have a curved surface 18b having an arc shape similar to a shape of a portion of an outer shape of the liquid feeding tube 41 as shown in FIG. 30. With such a configuration, the base plate 18 can easily absorb heat from the liquid feeding tube 41 and hence, efficiency of cooling the LED 32 is improved.

Ninth Modification

Figure 31:
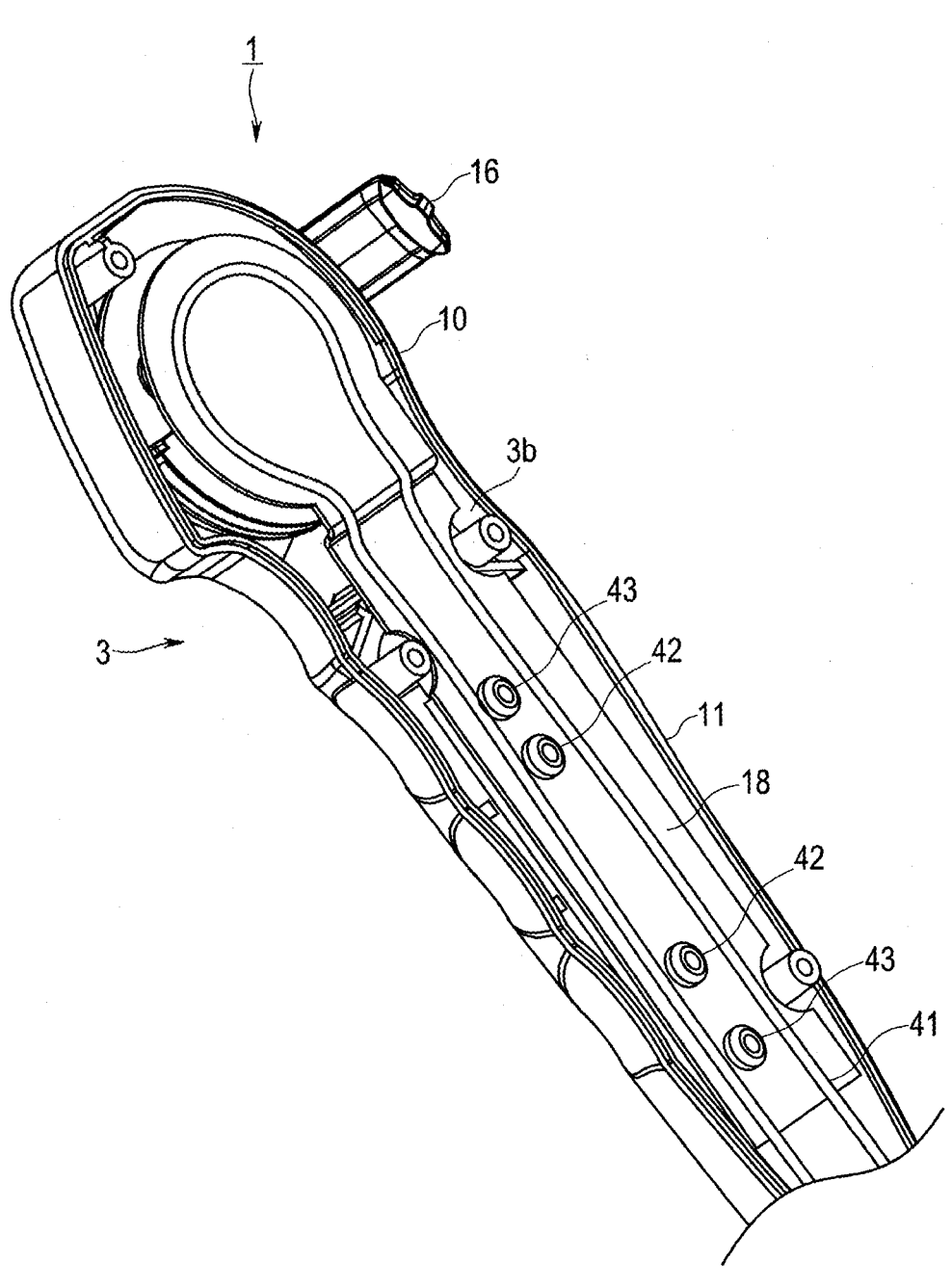
FIG. 31 is a perspective view, as viewed from a right side, partially showing an inside of an operation portion of an endoscope of a ninth modification, the operation portion being provided with a base plate with which the liquid feeding tube is in contact.

In the same manner as the eighth modification, as shown in FIG. 31, in an endoscope 1 of the present modification, the base plate 18, being a metal plate, is stacked on the substrate 31 of the light source apparatus 30 mounted in the operation portion 3. The liquid feeding tube 41 is not configured to be in contact with the fiber fixation block 33, but is disposed in such a way as to lie along and to be in contact with a surface of the base plate 18.

Figure 32:
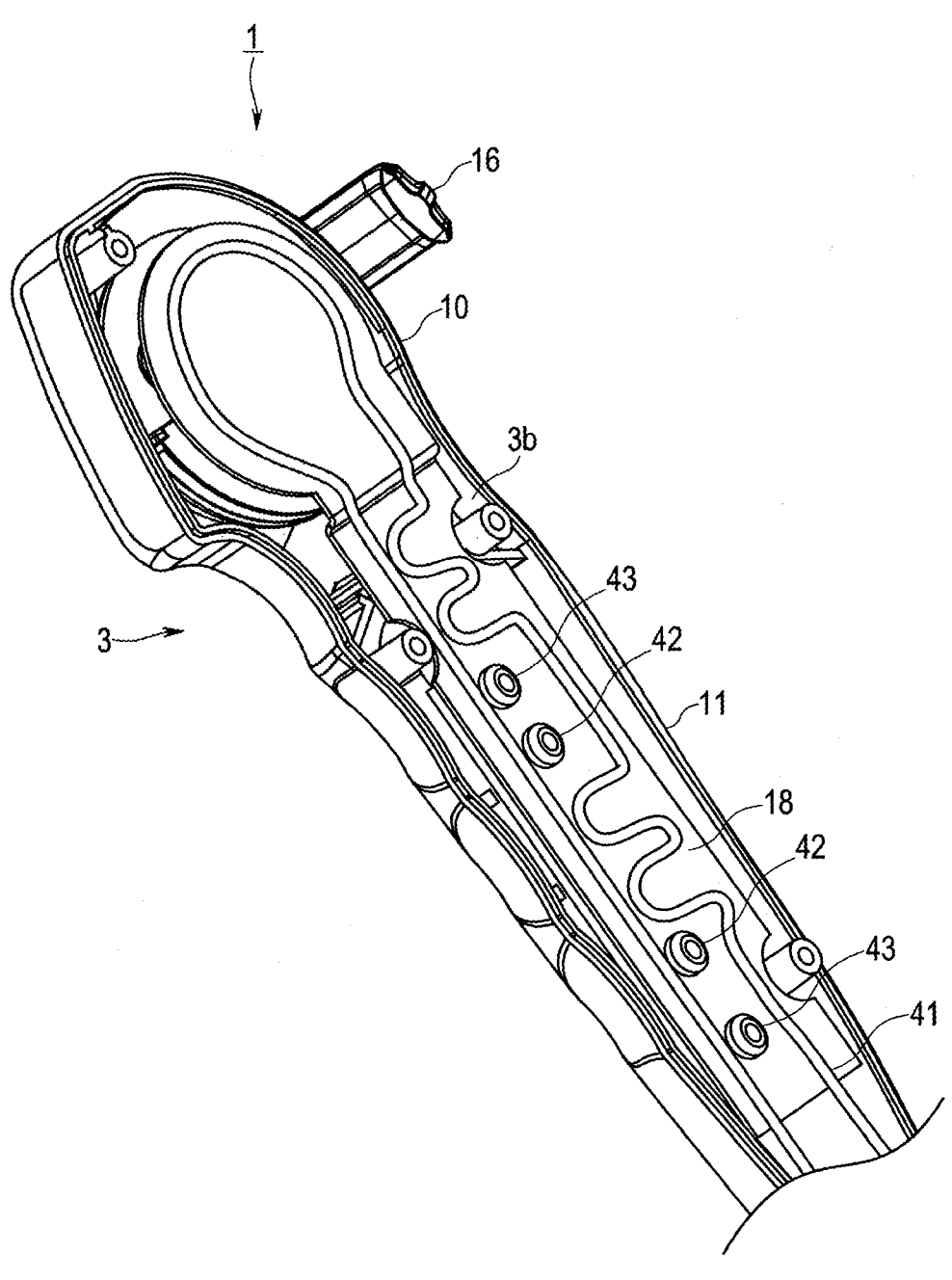
FIG. 32 is a perspective view, as viewed from a right side, partially showing the inside of the operation portion of the endoscope of the ninth modification in a state in which the operation portion is provided with the base plate with which the liquid feeding tube is in contact in a meandering manner.

The base plate 18 is cooled by the liquid feeding tube 41. The endoscope 1 has a large contact area between the base plate 18 and the liquid feeding tube 41 and hence, it is possible to improve efficiency of cooling the LED 32, being the heat source of the light source apparatus 30. The liquid feeding tube 41 may be caused to lie along the surface of the base plate 18 in a meandering manner as shown in FIG. 32.

Tenth Modification

Figure 33:
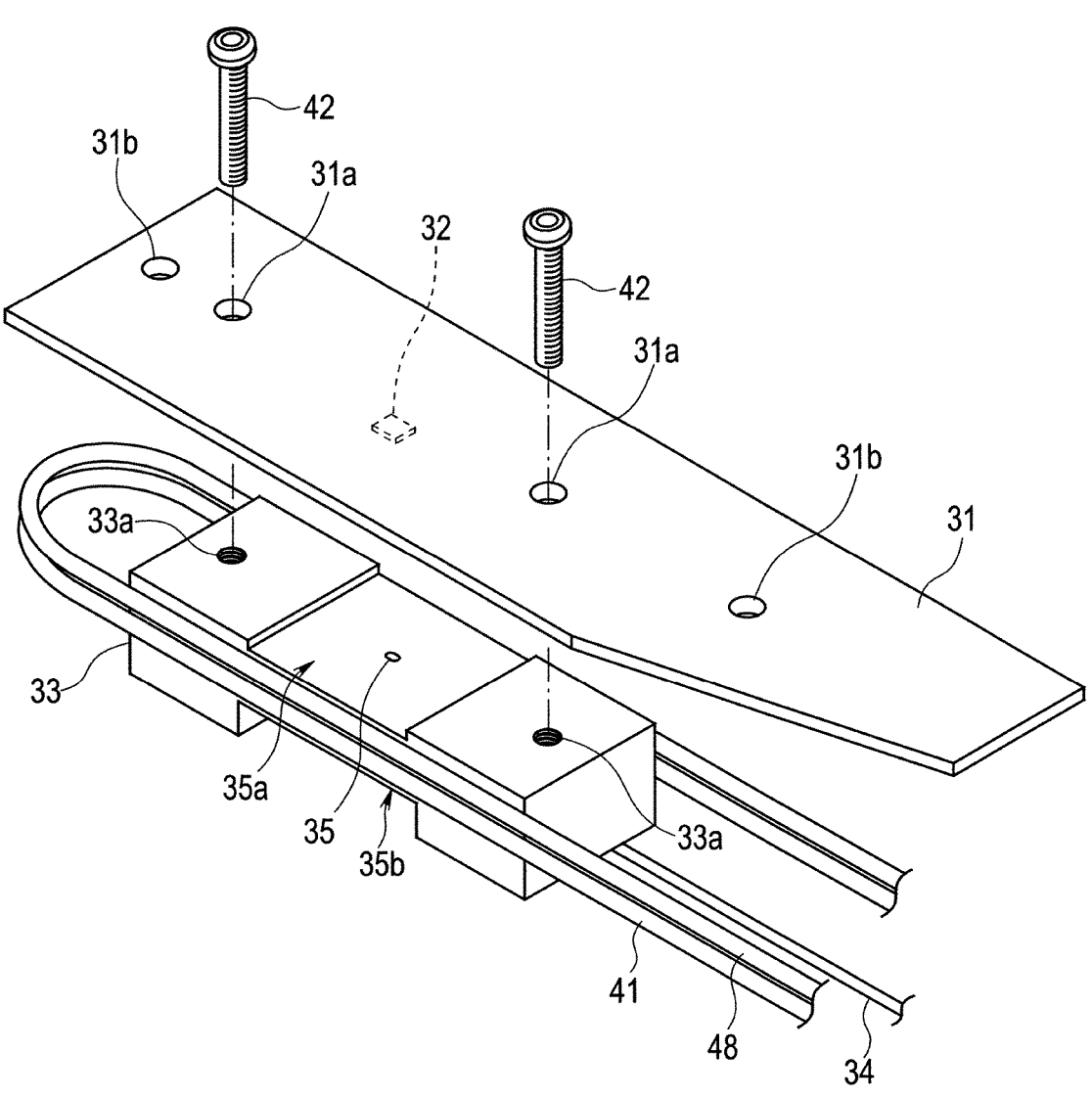
FIG. 33 is an exploded perspective view showing a light source apparatus of a tenth modification with which the liquid feeding tube and a suction tube are in contact.

As shown in FIG. 33, in an operation portion 3 of an endoscope 1 of the present modification, in addition to the liquid feeding tube 41, a suction tube 48 is disposed in such a way as to lie along and to be in contact with the side surfaces of the fiber fixation block 33 of the light source apparatus 30. The suction tube 48 is a suction channel connected to the accessory port (not shown) of the operation portion 3.

In the same manner as the liquid feeding tube 41, the suction tube 48 is a fluid conduit. The suction tube 48 is disposed in such a way as to surround the fiber fixation block 33 of the light source apparatus 30, is turned on the proximal end side of the operation portion 3, and then extends toward the distal end side.

In the same manner as the liquid feeding tube 41, an outer surface of the suction tube 48 may be in contact with the fiber fixation block 33 at least at one point or one part, or at a plurality of portions. Further, in the same manner as the liquid feeding tube 41, the suction tube 48 may be wound around the fiber fixation block 33 such that the outer surface of the suction tube 48 is in contact with the plurality of side surfaces of the fiber fixation block 33.

Also, for the suction tube 48, a soft bendable conduit made of PTFE (polytetrafluoroethylene) or PVC (polyvinyl chloride) is used in the same manner as the liquid feeding tube 41.

Further, the suction tube 48 may have the configuration of the sixth modification in which the tube is in contact with the LED 32, may have the configuration of the seventh modification in which the tube is disposed in such a way as to lie along the substrate 31, or may have the configuration of the ninth modification in which the tube is disposed in such a way as to lie along the base plate 18. The liquid feeding tube 41 and the suction tube 48 may be disposed such that either the liquid feeding tube 41 or the suction tube 48 is in contact with the fiber fixation block 33 or the base plate 18.

As described above, in the endoscope 1, not only when liquid is fed into the subject, but also when liquid is discharged to the outside of the subject, it is possible to cool the LED 32, being the heat source of the light source apparatus 30. The endoscope 1 of the present modification has a configuration effective for a ureteroscope (video uretero-renoscope) having a perfusion function of performing feeding and suction of liquid simultaneously.

The endoscope 1 may be configured such that instead of the liquid feeding tube 41, only the suction tube 48 cools the LED 32 of the light source apparatus 30.

Eleventh Modification

Figure 34:
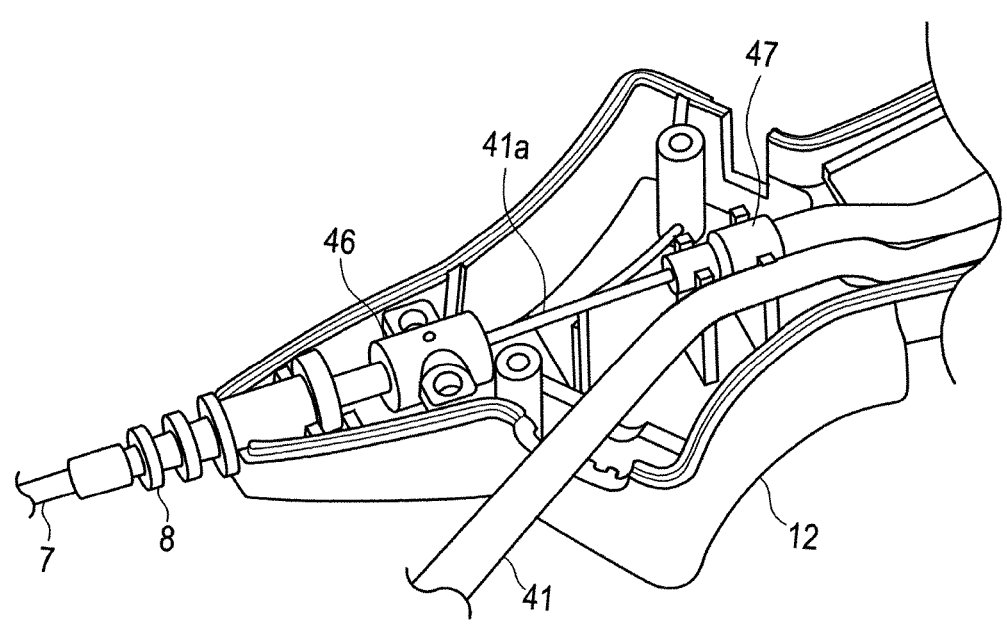
FIG. 34 is a perspective view partially showing an inside of an operation portion of an endoscope of an eleventh modification, the operation portion including a liquid feeding tube having a large diameter and a liquid feeding tube having a small diameter.

In the present modification, as shown in FIG. 34, a large-diameter tube body is used for a liquid feeding tube 41. The liquid feeding tube 41 is disposed in such a way as to lie in the operation portion 3 and, thereafter, is connected to a tube connecting pipe sleeve 47 fixed to the third operation portion 12. A liquid feeding tube 41a having a diameter smaller than a diameter of the liquid feeding tube 41 is connected to the tube connecting pipe sleeve 47.

The liquid feeding tube 41a having a small diameter is disposed in such a way as to be inserted through in the insertion portion 2 and to extend to the distal end portion 5. As described above, the liquid feeding tube 41 has a large diameter, and the liquid feeding tube 41a has a small diameter. At a portion in which the LED 32 of the light source apparatus 30 is cooled, a large contact area between the liquid feeding tube 41 having a large diameter and the light source apparatus 30 is set. On the other hand, the liquid feeding tube 41a having a small diameter is disposed in the insertion portion 2 and hence, it is possible to reduce an outer diameter of the insertion portion 2.

The endoscope 1 may be configured such that a dedicated cooling tube for cooling the light source apparatus 30 is provided, and a fluid, such as water, is caused to circulate through the cooling tube. In other words, the endoscope 1 may be configured to have a dedicated liquid-cooling function of cooling the light source apparatus 30 by absorbing heat of the LED 32 of the light source apparatus 30. The endoscope 1 can continuously circulate the fluid between an inside of a subject and an outside of the subject.

The disclosures described in the above-mentioned embodiment and modifications are not limited by such an embodiment and modifications, and various modifications are conceivable in the implementation stage without departing from the gist of the disclosures. Further, the above-described embodiment and modifications include disclosures at various stages, and various disclosures may be extracted by an appropriate combination of a plurality of components disclosed.

For example, even if some components are deleted from all components shown in the embodiment or the modification, a configuration from which some components are deleted may be extracted as the disclosure provided that the configuration can solve the problem described and can obtain effects described.

What is claimed is:

1. An insertion instrument, comprising:
   an insertion portion; and an operation portion located proximally relative to the insertion portion,
wherein the operation portion includes:
   a housing having an exterior body,
   a heat sink block located inside the exterior body,
   a substrate with a light emission body arranged to make contact with one surface of the heat sink block, and
   a conduit for a fluid, and
wherein the conduit includes:
   a first portion located outside the exterior body, and
   a second portion located inside the exterior body and in contact with an outer surface of the heat sink block.

2. The insertion instrument according to claim 1, wherein an outer surface of the second portion of the conduit is in contact with the heat sink block.

3. The insertion instrument according to claim 2, wherein a surface of the exterior body facing toward an interior of the housing includes a seating surface, and
   wherein the heat sink block and the second portion of the conduit are located in the seating surface with the second portion of the conduit located between a surface of the seating surface and a portion of the heat sink block.

4. The insertion instrument according to claim 1, further comprising a light guide,
   wherein the light guide transmits light from the light emission body to a light emission window of the insertion portion, and
   wherein a proximal end portion of the light guide is attached to the heat sink block.

5. The insertion instrument according to claim 4, wherein the light emission body and the light guide are attached to the heat sink block with the light emission body facing the proximal end of the light guide.

6. The insertion instrument according to claim 5, wherein the conduit is in contact with two or more surfaces of the heat sink block.

7. The insertion instrument according to claim 5, wherein the outer surface of the heat sink block includes a groove, and
   wherein the conduit is seated in the groove.

8. The insertion instrument according to claim 7, wherein the groove extends over only a portion of an outer surface of the second portion of the conduit.

9. The insertion instrument according to claim 4, wherein the light guide includes one or more optical fibers.

10. The insertion instrument according to claim 9, wherein the light emission body includes a light emitting diode or a semiconductor laser.

11. The insertion instrument according to claim 1, wherein the conduit further includes a third portion,
   wherein the third portion is formed by a channel in a body of the heat sink block, the heat sink block having a first connecting portion at a first end of the channel and a second connecting portion at a second end of the channel, and
   wherein third second portion of the conduit is located between the first portion and the third portion and connected to the first connecting portion and the second connecting portion.

12. The insertion instrument according to claim 1, wherein the exterior body includes:
   a first operation section,
   a second operation section including a handhold configured for grasping by an operator, and
   a plurality of vent holes providing a ventilation path from inside the housing to outside the housing, wherein the plurality of vent holes is located in at least one of (i) the first operation section and (ii) a portion of the second operation section other than the handhold, and wherein the housing includes an angle lever configured to operate the insertion portion, the angle lever located in the first operation section.

13. The insertion instrument according to claim 1, wherein the heat sink block covers a part of an outer surface of the second portion of the conduit.

14. The insertion instrument according to claim 1, wherein the light emission body includes one or more light emitting diodes, and wherein the second portion of the conduit contacts the light emitting diodes.

15. The insertion instrument according to claim 1, wherein the insertion instrument is an endoscope, and wherein the endoscope is configured to continuously circulate the fluid between an inside of a subject and an outside of the subject.

16. The insertion instrument according to claim 15, wherein the conduit is a flow path to supply the fluid to the inside of the subject, wherein the insertion instrument further comprises a suction tube configured to suction the fluid from the inside of the subject to the outside of the subject, and wherein a first portion of the suction tube is located in the exterior body of the housing, and at least a part of the first portion of the suction tube contacts the outer surface of the heat sink block.

17. The insertion instrument according to claim 1, further comprising a base plate attached to the substrate, wherein the second portion of the conduit contacts the base plate.

18. The insertion instrument according to claim 1, wherein the second portion of the conduit is a tube arranged to contact the outer surface of the heat sink block.

19. The insertion instrument according to claim 1, wherein the substrate is attached to the heat sink block so that the light emission body is positioned opposite to the one surface of the heat sink block.

20. The insertion instrument according to claim 19, wherein the heat sink block is provided with a recess on the one surface, and the light emission body is arranged in the recess.

* * * * *